(12) United States Patent
Bielicki

(10) Patent No.: US 7,217,785 B2
(45) Date of Patent: May 15, 2007

(54) CYSTEINE-CONTAINING PEPTIDES HAVING ANTIOXIDANT PROPERTIES

(75) Inventor: John K. Bielicki, Castro Valley, CA (US)

(73) Assignee: The Regents of The University of California, Oakland, CA (US)

(*) Notice: Subject to any disclaimer, the term of this patent is extended or adjusted under 35 U.S.C. 154(b) by 33 days.

(21) Appl. No.: 10/142,238

(22) Filed: May 8, 2002

(65) Prior Publication Data

US 2003/0087819 A1 May 8, 2003

Related U.S. Application Data

(60) Provisional application No. 60/289,944, filed on May 9, 2001.

(51) Int. Cl.
C07K 14/00 (2006.01)
C07K 2/00 (2006.01)
C07K 1/00 (2006.01)
C07K 7/00 (2006.01)
A61K 38/00 (2006.01)
A61K 38/02 (2006.01)
A61K 38/16 (2006.01)

(52) U.S. Cl. .............. 530/324; 530/300; 530/333; 514/2; 514/12

(58) Field of Classification Search ........... 530/300, 530/324
See application file for complete search history.

(56) References Cited

U.S. PATENT DOCUMENTS

| | | | |
|---|---|---|---|
| 4,643,988 | A | 2/1987 | Segrest et al. |
| 5,721,114 | A | 2/1998 | Abrahamsen et al. |
| 5,733,549 | A | 3/1998 | Yamada et al. |
| 5,876,968 | A | 3/1999 | Sirtori et al. |
| 5,955,055 | A | 9/1999 | Lees et al. |
| 6,156,727 | A | 12/2000 | Garber et al. |
| 6,258,596 | B1 | 7/2001 | Benoit et al. |
| 6,596,544 | B1 | 7/2003 | Fogelman et al. |
| 6,617,156 | B1 | 9/2003 | Doucette-Stamm et al. |
| 6,635,623 | B1 | 10/2003 | Hoogeveen et al. |
| 6,734,169 | B2 | 5/2004 | Dasseux et al. |
| 2005/0196754 | A1* | 9/2005 | Drmanac et al. ............ 435/6 |

OTHER PUBLICATIONS

J Rudinger. In: Peptide Hormones, JA Parsons, Ed. (1976) 1-7.*
SIGMA. Designing Custom Peptides. http://www.sigma-genosys.com/peptide_design.asp (Accessed Dec. 16, 2004). 2 pages.*
HJC Berendsen. A Glimpse of the Holy Grail? Science (1998) 282. 642-643.*
D Voet and JG Voet. Biochemistry, 2nd Edition.(1995). 235-241.*
KH Weisgraber, et al. Apolipoprotein A-IMilano. J Biol Chem (1983) 285(1). 2508-2513.*
G Utermann, et al. Eur. J. Biochem. (1984) 144. 325-331.*
NCBI GenBank Accession No. NP_44320. accessed at http://www.ncbi.nlm.nih.gov/gquery/gquery.fcgi. Accessed Feb. 10, 2005. 1 page.*
NCBI GenBank Accession No. XP_043694. accessed at http://www.ncbi.nlm.nih.gov/entrez/sutils/girevhist.cgi?val=XP_043694. Accessed Feb. 10, 2005. 3 pages.*
Datta, et al.; "Aromatic Residue on the Nonpolar Face of Class A Amphipathic Helical Peptides Determines Biological Activity;" The Journal of Biological Chemistry; Jun. 18, 2004; pp. 26509-26517; vol. 279; No. 24; The American Society for Biochemistry and Molecular Biology, Inc.; USA.
Jia, et al.; "Thiol-bearing Synthetic Peptides Retain the Antioxidant Activity of ApolipoproteinA-I(Milano);" Biochemical and Biophysical Research Communications; Sep. 20, 2002; pp. 206-213; vol. 297; Issue 2; Elsevier Science.
Navab, et al.; "Thematic Review Series: The Pathogenesis of Atherosclerosis; The Oxidation Hypothesis of Atherogenesis: The Role of Oxidized Phospholipids and HDL;"; Journal of Lipid Research; Apr. 1, 2004; pp. 993-1007; vol. 45; The American Society for Biochemistry and Molecular Biology, Inc.
Reddy, et al. "ATP-Binding Cassette Transporter 1 Participates in LDL Oxidation by Artery Wall Cells;" Arterioscler Thromb Vasc Biol.; Nov. 2002; pp. 1877-1883; vol. 22.
Schmitz, et al.; "ATP-Binding Cassette Transporter A1 (ABCA1) in Macrophages: A Dual Function in Inflammation and Lipid Metabolism?;" Pathobiology; 2000; pp. 236-240; vol. 67; Karger AG; Basel.
Sean Ameli et al., "Recombinant Apolipoprotein A-I Milano Reduces Intimal Thickening After Balloon Injury in Hypercholesterolemic Rabbits," Circulation, 90, 4:1935-1941, (Oct. 13, 1994).
Gerd Assman et al., "High Density Lipoproteins, Reverse Transport of Choloesterol, and Coronary Artery Disease," Circulation, vol. 87 (No. 4), p. III-28-34, (Apr. 13, 1993).
John K. Bielicki et al., "Apolipoprotein A-IMilano and Apolipoprotein A-iParis Exhibit an Antioxidant Activity Distinct from That of Wild-type Apolipoprotein A-I," Biochemistry, 41:2089-2096, (Jan. 2002).

(Continued)

Primary Examiner—Cecilia J. Tsang
Assistant Examiner—Andrew D. Kosar
(74) Attorney, Agent, or Firm—Townsend and Townsend and Crew LLP

(57) ABSTRACT

The term "homology" or "homologous" means an amino acid similarity measured by the program, BLAST (Altschul et al (1997), "Gapped BLAST and PSI-BLAST: a new generation of protein database search programs", Nucleic Acids Res. 25:33 89–3402), and expressed as —(% identity n/n). In measuring homology between a peptide and a protein of greater size, homology is measured only in the corresponding region; that is, the protein is regarded as only having the same general length as the peptide, allowing for gaps and insertions.

6 Claims, 11 Drawing Sheets

OTHER PUBLICATIONS

Eric Bruckert et al, "The replacement of arginine by cysteine at residue 151 in Apolipoprotein A-I produces a phenotype similar to that of Apolipoprotein A-IMilano," Atherosclerosis, 128:121-128, (1997).

Robert J. Brushia et al., "Baculovirus-mediated expression and purification of human serum paraoxonase 1A," Journal of Lipid Research, 42: 951-958, (Jun. 2001).

Guido Franceschini et al., "A-IMilano Apoprotein: Decreased High Density Lipoprotein Cholesterol Levels with Significant Lipoprotein Modifications and Without Clinical Atherosclerosis in an Italian Family," J. Clin. Invest., 66:892-900, (Nov. 1980).

Guido Franceschini et al., "Apolipoprotein A-I Milano: Accelerated Binding and Dissociation From Lipids of a Human Apolipoprotein Variant," J. Biol. Chem. 260, 30:16321-16325, (Dec. 1985).

David W. Garber et al., "A New Synthetic class A Amphipathic peptide analogue protects mice from diet-induced atherosclerosis," Journal of Lipid Research, 42: 545-552, (Apr. 2001).

Kristin L. Gillotte et al., "Apolipoprotein-mediated Plasma Membrane Microsolubilization," Journal of Biological Chemistry, vol. 272 (No. 4), p. 2021-2028, (Jan. 1999).

Armando J. Mendez et al., "Synthetic Amphipathic Helical Peptides That Mimic Apolipoprotein A-I in Cleaning Cellular Cholesterol," J. Clin, Invest., 94:1698-1705, (Oct. 1994).

Vinod K. Mishra et al., "Studies of Synthetic Peptides of Human Apoloprotein A-I Containing Tandem Amphipathic alpha-Helixes," Biochemistry, 37: 10313-1032, (June 25, 1998).

Michael N. Oda et al., "Cysteine Substitutions in Apolipoprotein A-I Primary Structure Modulate Paraoxonase Activity," Biochemistry, 40:1710-1718, (Jan. 19, 2001).

Palgunachari et al., "Only the Two End Helixes of Eight Tandem Amphipathic Helical Domains of Human Apo A-I Have Significant Lipid Affinity," Arteriosclerosis, Thrombosis, and Vascular Biology, 16, 2:328-338, (Feb. 13, 1996).

Oscar Perez-Mendez et al., "Metabolism of Apolipoproteins AI and AII in subjects carrying similar apoAI mutations, apoAI Milano and apoAI PAris," Atherosclerosis, 148: 317-326, (2000).

Basil M. Rifkind, "High-Density Lipoprotein Cholesterol and Coronary Artery Disease:Survey of the Evidence," The Americal Journal of Cardiology, 66: 3A-6A, ( Sep. 4, 1990).

Prediman K. Shah et al., "High-dose Recombinant Apolipoprotein A-I Milano Mobilizes Tissue Cholesterol and Rapidly Reduces Plaque Lipid and Macrophage Content in Apolipoprotein E-Deficient Mice," Circulation, 103:3047-3050, (Jun. 2001).

Prediman K. Shah et al., "Effects of Recombinant Apolipoprotein A-I Milano on Aortic Atherosclerosis in Apolipoprotein E-Deficient Mice," Circulation, 97:780-785, (Mar. 1998).

Cesare R. Sirtori et al., "Cardiovascular Status of Carriers of the Apolipoprotein A-I Milano Mutant: The Limone sul Garda Study," Circulation, 103:1949-1954, ( Apr. 2001).

M.G. Sorci-Thomas et al., "Alteration in apolipoprotein A-I 22-mer repeat order results in a decrease in lecithin:cholesterol acyltransferase reactivity," J. Bio. Chem., 272:7278-7284, (Mar. 14, 1997).

M.G. Sorci-Thomas et al., "The hydrophobic face orientation of apolipoprotein A-I amphipathic helix domain 143-164 regulates lecithin-cholesterol acyltransferase activation," J. Bio. Chem., 273:11776-11782, (May 8, 1998).

Peter W.F. Wilson, "High-Density Lipoprotein, Low-Density Lipoprotein and Coronary Artery Disease," Am J Cardiol, 66:7A-10A, (Sep. 4, 1990).

Karl H. Weisgraber et al., "A-I Milano Apoprotein: Isolation and Characterization of Cysteine-containing Variant of the A-I Apoprotein from Human High Density Lipoproteins," J. Clin. Invest., 66: 901-907, (Nov. 13, 1980).

Karl H. Weisgraber, "Apolipoprotein A-I Milano: Detection of Normal A-I in Affected Subjects and Evidence for a Cysteine for Arginine Substitution in the Variant A-I," J.Biol. Chem., 258 4:2508-2513, (Feb. 1983).

* cited by examiner

Figure 1: ApoA-I Peptide Mimetics

Figure 3: ApoAV Peptide Mimetics

Figure 4: Oxidation Protection Assays

Generalized placement of cysteine (*) within peptide mimetics:

Generalized placement of cysteine (✱) within peptide mimetics:

SEQUENCE LISTING

<160> NUMBER OF SEQ ID NOS: 84

<210> SEQ ID NO 1
<211> LENGTH: 18
<212> TYPE: PRT
<213> ORGANISM: ARTIFICIAL SEQUENCE
<220> FEATURE:
<221> NAME/KEY: PEPTIDE
<222> LOCATION: (1)..(18)
<223> OTHER INFORMATION: HUMAN GENETIC ORIGIN

<400> SEQUENCE: 1

Ser Asp Glu Leu Arg Gln Cys Leu Ala Ala Arg Leu Glu Ala Leu Lys
1               5                   10                  15

Glu Asn

<210> SEQ ID NO 2
<211> LENGTH: 18
<212> TYPE: PRT
<213> ORGANISM: ARTIFICIAL SEQUENCE
<220> FEATURE:
<221> NAME/KEY: PEPTIDE
<222> LOCATION: (1)..(18)
<223> OTHER INFORMATION: HUMAN GENETIC ORIGIN

<400> SEQUENCE: 2

Ser Asp Glu Leu Arg Gln Arg Leu Ala Ala Arg Leu Glu Ala Leu Lys
1               5                   10                  15

Glu Asn

<210> SEQ ID NO 3
<211> LENGTH: 18
<212> TYPE: PRT
<213> ORGANISM: ARTIFICIAL SEQUENCE
<220> FEATURE:
<221> NAME/KEY: PEPTIDE
<222> LOCATION: (1)..(18)
<223> OTHER INFORMATION: HUMAN GENETIC ORIGIN

<400> SEQUENCE: 3

Ser Asp Glu Leu Cys Gln Arg Leu Ala Ala Arg Leu Glu Ala Leu Lys
1               5                   10                  15

Glu Asn

<210> SEQ ID NO 4
<211> LENGTH: 18
<212> TYPE: PRT
<213> ORGANISM: ARTIFICIAL SEQUENCE
<220> FEATURE:
<221> NAME/KEY: PEPTIDE
<222> LOCATION: (1)..(18)
<223> OTHER INFORMATION: HUMAN GENETIC ORIGIN

<400> SEQUENCE: 4

Ser Asp Glu Leu Arg Cys Arg Leu Ala Ala Arg Leu Glu Ala Leu Lys
1               5                   10                  15

Glu Asn

<210> SEQ ID NO 5
<211> LENGTH: 18
<212> TYPE: PRT
<213> ORGANISM: ARTIFICIAL SEQUENCE
<220> FEATURE:
<221> NAME/KEY: PEPTIDE

```
<222> LOCATION: (1)..(18)
<223> OTHER INFORMATION: HUMAN GENETIC ORIGIN

<400> SEQUENCE: 5

Ser Asp Glu Leu Arg Gln Arg Cys Ala Ala Arg Leu Glu Ala Leu Lys
1               5                   10                  15

Glu Asn

<210> SEQ ID NO 6
<211> LENGTH: 18
<212> TYPE: PRT
<213> ORGANISM: ARTIFICIAL SEQUENCE
<220> FEATURE:
<221> NAME/KEY: PEPTIDE
<222> LOCATION: (1)..(18)
<223> OTHER INFORMATION: HUMAN GENETIC ORIGIN

<400> SEQUENCE: 6

Ser Asp Glu Leu Arg Gln Arg Leu Cys Ala Arg Leu Glu Ala Leu Lys
1               5                   10                  15

Glu Asn

<210> SEQ ID NO 7
<211> LENGTH: 18
<212> TYPE: PRT
<213> ORGANISM: ARTIFICIAL SEQUENCE
<220> FEATURE:
<221> NAME/KEY: PEPTIDE
<222> LOCATION: (1)..(18)
<223> OTHER INFORMATION: HUMAN GENETIC ORIGIN

<400> SEQUENCE: 7

Ser Asp Glu Leu Arg Gln Arg Leu Ala Cys Arg Leu Glu Ala Leu Lys
1               5                   10                  15

Glu Asn

<210> SEQ ID NO 8
<211> LENGTH: 18
<212> TYPE: PRT
<213> ORGANISM: ARTIFICIAL SEQUENCE
<220> FEATURE:
<221> NAME/KEY: PEPTIDE
<222> LOCATION: (1)..(18)
<223> OTHER INFORMATION: HUMAN GENETIC ORIGIN

<400> SEQUENCE: 8

Ser Asp Glu Leu Arg Gln Arg Leu Ala Ala Arg Leu Glu Ala Cys Lys
1               5                   10                  15

Glu Asn

<210> SEQ ID NO 9
<211> LENGTH: 18
<212> TYPE: PRT
<213> ORGANISM: ARTIFICIAL SEQUENCE
<220> FEATURE:
<221> NAME/KEY: PEPTIDE
<222> LOCATION: (1)..(18)
<223> OTHER INFORMATION: HUMAN GENETIC ORIGIN

<400> SEQUENCE: 9

Gly Glu Glu Met Arg Asp Cys Ala Arg Ala His Val Asp Ala Leu Arg
1               5                   10                  15

Thr His
```

<210> SEQ ID NO 10
<211> LENGTH: 18
<212> TYPE: PRT
<213> ORGANISM: ARTIFICIAL SEQUENCE
<220> FEATURE:
<221> NAME/KEY: PEPTIDE
<222> LOCATION: (1)..(18)
<223> OTHER INFORMATION: HUMAN GENETIC ORIGIN

<400> SEQUENCE: 10

Gly Glu Glu Met Arg Asp Arg Ala Arg Ala His Val Asp Ala Leu Arg
1               5                   10                  15

Thr His

<210> SEQ ID NO 11
<211> LENGTH: 18
<212> TYPE: PRT
<213> ORGANISM: ARTIFICIAL SEQUENCE
<220> FEATURE:
<221> NAME/KEY: PEPTIDE
<222> LOCATION: (1)..(18)
<223> OTHER INFORMATION: HUMAN GENETIC ORIGIN

<400> SEQUENCE: 11

Gly Glu Glu Met Cys Asp Arg Ala Arg Ala His Val Asp Ala Leu Arg
1               5                   10                  15

Thr His

<210> SEQ ID NO 12
<211> LENGTH: 18
<212> TYPE: PRT
<213> ORGANISM: ARTIFICIAL SEQUENCE
<220> FEATURE:
<221> NAME/KEY: PEPTIDE
<222> LOCATION: (1)..(18)
<223> OTHER INFORMATION: HUMAN GENETIC ORIGIN

<400> SEQUENCE: 12

Gly Glu Glu Met Arg Cys Arg Ala Arg Ala His Val Asp Ala Leu Arg
1               5                   10                  15

Thr His

<210> SEQ ID NO 13
<211> LENGTH: 18
<212> TYPE: PRT
<213> ORGANISM: ARTIFICIAL SEQUENCE
<220> FEATURE:
<221> NAME/KEY: PEPTIDE
<222> LOCATION: (1)..(18)
<223> OTHER INFORMATION: HUMAN GENETIC ORIGIN

<400> SEQUENCE: 13

Gly Glu Glu Met Arg Asp Arg Cys Arg Ala His Val Asp Ala Leu Arg
1               5                   10                  15

Thr His

<210> SEQ ID NO 14
<211> LENGTH: 18
<212> TYPE: PRT
<213> ORGANISM: ARTIFICIAL SEQUENCE
<220> FEATURE:
<221> NAME/KEY: PEPTIDE
<222> LOCATION: (1)..(18)
<223> OTHER INFORMATION: HUMAN GENETIC ORIGIN

<400> SEQUENCE: 14

Gly Glu Glu Met Arg Asp Arg Ala Cys Ala His Val Asp Ala Leu Arg
1               5                   10                  15

Thr His

<210> SEQ ID NO 15
<211> LENGTH: 18
<212> TYPE: PRT
<213> ORGANISM: ARTIFICIAL SEQUENCE
<220> FEATURE:
<221> NAME/KEY: PEPTIDE
<222> LOCATION: (1)..(18)
<223> OTHER INFORMATION: HUMAN GENETIC ORIGIN

<400> SEQUENCE: 15

Gly Glu Glu Met Arg Asp Arg Ala Arg Ala Cys Val Asp Ala Leu Arg
1               5                   10                  15

Thr His

<210> SEQ ID NO 16
<211> LENGTH: 18
<212> TYPE: PRT
<213> ORGANISM: ARTIFICIAL SEQUENCE
<220> FEATURE:
<221> NAME/KEY: PEPTIDE
<222> LOCATION: (1)..(18)
<223> OTHER INFORMATION: HUMAN GENETIC ORIGIN

<400> SEQUENCE: 16

Pro Val Leu Glu Ser Phe Cys Val Ser Phe Leu Ser Ala Leu Glu Glu
1               5                   10                  15

Tyr Thr

<210> SEQ ID NO 17
<211> LENGTH: 18
<212> TYPE: PRT
<213> ORGANISM: ARTIFICIAL SEQUENCE
<220> FEATURE:
<221> NAME/KEY: PEPTIDE
<222> LOCATION: (1)..(18)
<223> OTHER INFORMATION: HUMAN GENETIC ORIGIN

<400> SEQUENCE: 17

Pro Val Leu Glu Ser Phe Lys Val Ser Phe Leu Ser Ala Leu Glu Glu
1               5                   10                  15

Tyr Thr

<210> SEQ ID NO 18
<211> LENGTH: 18
<212> TYPE: PRT
<213> ORGANISM: ARTIFICIAL SEQUENCE
<220> FEATURE:
<221> NAME/KEY: PEPTIDE
<222> LOCATION: (1)..(18)
<223> OTHER INFORMATION: HUMAN GENETIC ORIGIN

<400> SEQUENCE: 18

Pro Val Leu Cys Ser Phe Lys Val Ser Phe Leu Ser Ala Leu Glu Glu
1               5                   10                  15

Tyr Thr

<210> SEQ ID NO 19
<211> LENGTH: 18
<212> TYPE: PRT
<213> ORGANISM: ARTIFICIAL SEQUENCE
<220> FEATURE:

```
<221> NAME/KEY: PEPTIDE
<222> LOCATION: (1)..(18)
<223> OTHER INFORMATION: HUMAN GENETIC ORIGIN

<400> SEQUENCE: 19

Pro Val Leu Glu Cys Phe Lys Val Ser Phe Leu Ser Ala Leu Glu Glu
1               5                   10                  15

Tyr Thr

<210> SEQ ID NO 20
<211> LENGTH: 18
<212> TYPE: PRT
<213> ORGANISM: ARTIFICIAL SEQUENCE
<220> FEATURE:
<221> NAME/KEY: PEPTIDE
<222> LOCATION: (1)..(18)
<223> OTHER INFORMATION: HUMAN GENETIC ORIGIN

<400> SEQUENCE: 20

Pro Val Leu Glu Ser Cys Lys Val Ser Phe Leu Ser Ala Leu Glu Glu
1               5                   10                  15

Tyr Thr

<210> SEQ ID NO 21
<211> LENGTH: 18
<212> TYPE: PRT
<213> ORGANISM: ARTIFICIAL SEQUENCE
<220> FEATURE:
<221> NAME/KEY: PEPTIDE
<222> LOCATION: (1)..(18)
<223> OTHER INFORMATION: HUMAN GENETIC ORIGIN

<400> SEQUENCE: 21

Pro Val Leu Glu Ser Phe Lys Cys Ser Phe Leu Ser Ala Leu Glu Glu
1               5                   10                  15

Tyr Thr

<210> SEQ ID NO 22
<211> LENGTH: 18
<212> TYPE: PRT
<213> ORGANISM: ARTIFICIAL SEQUENCE
<220> FEATURE:
<221> NAME/KEY: PEPTIDE
<222> LOCATION: (1)..(18)
<223> OTHER INFORMATION: HUMAN GENETIC ORIGIN

<400> SEQUENCE: 22

Pro Val Leu Glu Ser Phe Lys Val Cys Phe Leu Ser Ala Leu Glu Glu
1               5                   10                  15

Tyr Thr

<210> SEQ ID NO 23
<211> LENGTH: 18
<212> TYPE: PRT
<213> ORGANISM: ARTIFICIAL SEQUENCE
<220> FEATURE:
<221> NAME/KEY: PEPTIDE
<222> LOCATION: (1)..(18)
<223> OTHER INFORMATION: HUMAN GENETIC ORIGIN

<400> SEQUENCE: 23

Pro Val Leu Glu Ser Phe Lys Val Ser Cys Leu Ser Ala Leu Glu Glu
1               5                   10                  15

Tyr Thr
```

```
<210> SEQ ID NO 24
<211> LENGTH: 18
<212> TYPE: PRT
<213> ORGANISM: ARTIFICIAL SEQUENCE
<220> FEATURE:
<221> NAME/KEY: PEPTIDE
<222> LOCATION: (1)..(18)
<223> OTHER INFORMATION: HUMAN GENETIC ORIGIN

<400> SEQUENCE: 24

Pro Val Leu Glu Ser Phe Lys Val Ser Phe Cys Ser Ala Leu Glu Glu
1               5                   10                  15

Tyr Thr

<210> SEQ ID NO 25
<211> LENGTH: 18
<212> TYPE: PRT
<213> ORGANISM: ARTIFICIAL SEQUENCE
<220> FEATURE:
<221> NAME/KEY: PEPTIDE
<222> LOCATION: (1)..(18)
<223> OTHER INFORMATION: HUMAN GENETIC ORIGIN

<400> SEQUENCE: 25

Pro Val Leu Glu Ser Phe Lys Val Ser Phe Leu Cys Ala Leu Glu Glu
1               5                   10                  15

Tyr Thr

<210> SEQ ID NO 26
<211> LENGTH: 18
<212> TYPE: PRT
<213> ORGANISM: ARTIFICIAL SEQUENCE
<220> FEATURE:
<221> NAME/KEY: PEPTIDE
<222> LOCATION: (1)..(18)
<223> OTHER INFORMATION: HUMAN GENETIC ORIGIN

<400> SEQUENCE: 26

Pro Val Leu Glu Ser Phe Lys Val Ser Phe Leu Ser Cys Leu Glu Glu
1               5                   10                  15

Tyr Thr

<210> SEQ ID NO 27
<211> LENGTH: 18
<212> TYPE: PRT
<213> ORGANISM: ARTIFICIAL SEQUENCE
<220> FEATURE:
<221> NAME/KEY: PEPTIDE
<222> LOCATION: (1)..(18)
<223> OTHER INFORMATION: HUMAN GENETIC ORIGIN

<400> SEQUENCE: 27

Pro Val Leu Glu Ser Phe Lys Val Ser Phe Leu Ser Ala Leu Cys Glu
1               5                   10                  15

Tyr Thr

<210> SEQ ID NO 28
<211> LENGTH: 18
<212> TYPE: PRT
<213> ORGANISM: ARTIFICIAL SEQUENCE
<220> FEATURE:
<221> NAME/KEY: PEPTIDE
<222> LOCATION: (1)..(18)
<223> OTHER INFORMATION: HUMAN GENETIC ORIGIN

<400> SEQUENCE: 28
```

Pro Val Leu Glu Ser Phe Lys Val Ser Phe Leu Ser Ala Leu Glu Cys
1               5                   10                  15

Tyr Thr

<210> SEQ ID NO 29
<211> LENGTH: 18
<212> TYPE: PRT
<213> ORGANISM: ARTIFICIAL SEQUENCE
<220> FEATURE:
<221> NAME/KEY: PEPTIDE
<222> LOCATION: (1)..(18)
<223> OTHER INFORMATION: HUMAN GENETIC ORIGIN

<400> SEQUENCE: 29

Pro Val Leu Glu Ser Phe Lys Val Ser Phe Leu Ser Ala Leu Glu Glu
1               5                   10                  15

Cys Thr

<210> SEQ ID NO 30
<211> LENGTH: 33
<212> TYPE: PRT
<213> ORGANISM: ARTIFICIAL SEQUENCE
<220> FEATURE:
<221> NAME/KEY: PEPTIDE
<222> LOCATION: (1)..(33)
<223> OTHER INFORMATION: HUMAN GENETIC ORIGIN

<400> SEQUENCE: 30

Pro Ala Leu Glu Asp Leu Arg Gln Gly Leu Leu Pro Val Leu Glu Ser
1               5                   10                  15

Phe Cys Val Ser Phe Leu Ser Ala Leu Glu Glu Tyr Thr Lys Lys Leu
            20                  25                  30

Asn

<210> SEQ ID NO 31
<211> LENGTH: 33
<212> TYPE: PRT
<213> ORGANISM: ARTIFICIAL SEQUENCE
<220> FEATURE:
<221> NAME/KEY: PEPTIDE
<222> LOCATION: (1)..(33)
<223> OTHER INFORMATION: HUMAN GENETIC ORIGIN

<400> SEQUENCE: 31

Pro Ala Leu Glu Asp Leu Arg Gln Gly Leu Leu Pro Val Leu Glu Ser
1               5                   10                  15

Phe Lys Val Ser Phe Leu Ser Ala Leu Glu Glu Tyr Thr Lys Lys Leu
            20                  25                  30

Asn

<210> SEQ ID NO 32
<211> LENGTH: 18
<212> TYPE: PRT
<213> ORGANISM: ARTIFICIAL SEQUENCE
<220> FEATURE:
<221> NAME/KEY: PEPTIDE
<222> LOCATION: (1)..(18)
<223> OTHER INFORMATION: HUMAN GENETIC ORIGIN

<400> SEQUENCE: 32

Leu Lys Leu Cys Asp Asn Trp Asp Ser Val Thr Ser Thr Phe Ser Lys
1               5                   10                  15

Leu Arg

```
<210> SEQ ID NO 33
<211> LENGTH: 18
<212> TYPE: PRT
<213> ORGANISM: ARTIFICIAL SEQUENCE
<220> FEATURE:
<221> NAME/KEY: PEPTIDE
<222> LOCATION: (1)..(18)
<223> OTHER INFORMATION: HUMAN GENETIC ORIGIN

<400> SEQUENCE: 33

Leu Lys Leu Leu Asp Asn Trp Asp Ser Val Thr Ser Thr Phe Ser Lys
 1               5                  10                  15

Leu Arg

<210> SEQ ID NO 34
<211> LENGTH: 18
<212> TYPE: PRT
<213> ORGANISM: ARTIFICIAL SEQUENCE
<220> FEATURE:
<221> NAME/KEY: PEPTIDE
<222> LOCATION: (1)..(18)
<223> OTHER INFORMATION: HUMAN GENETIC ORIGIN

<400> SEQUENCE: 34

Leu Cys Leu Leu Asp Asn Trp Asp Ser Val Thr Ser Thr Phe Ser Lys
 1               5                  10                  15

Leu Arg

<210> SEQ ID NO 35
<211> LENGTH: 18
<212> TYPE: PRT
<213> ORGANISM: ARTIFICIAL SEQUENCE
<220> FEATURE:
<221> NAME/KEY: PEPTIDE
<222> LOCATION: (1)..(18)
<223> OTHER INFORMATION: HUMAN GENETIC ORIGIN

<400> SEQUENCE: 35

Leu Lys Cys Leu Asp Asn Trp Asp Ser Val Thr Ser Thr Phe Ser Lys
 1               5                  10                  15

Leu Arg

<210> SEQ ID NO 36
<211> LENGTH: 18
<212> TYPE: PRT
<213> ORGANISM: ARTIFICIAL SEQUENCE
<220> FEATURE:
<221> NAME/KEY: PEPTIDE
<222> LOCATION: (1)..(18)
<223> OTHER INFORMATION: HUMAN GENETIC ORIGIN

<400> SEQUENCE: 36

Leu Lys Leu Leu Cys Asn Trp Asp Ser Val Thr Ser Thr Phe Ser Lys
 1               5                  10                  15

Leu Arg

<210> SEQ ID NO 37
<211> LENGTH: 18
<212> TYPE: PRT
<213> ORGANISM: ARTIFICIAL SEQUENCE
<220> FEATURE:
<221> NAME/KEY: PEPTIDE
<222> LOCATION: (1)..(18)
<223> OTHER INFORMATION: HUMAN GENETIC ORIGIN
```

```
<400> SEQUENCE: 37

Leu Lys Leu Leu Asp Cys Trp Asp Ser Val Thr Ser Thr Phe Ser Lys
1               5                   10                  15

Leu Arg

<210> SEQ ID NO 38
<211> LENGTH: 18
<212> TYPE: PRT
<213> ORGANISM: ARTIFICIAL SEQUENCE
<220> FEATURE:
<221> NAME/KEY: PEPTIDE
<222> LOCATION: (1)..(18)
<223> OTHER INFORMATION: HUMAN GENETIC ORIGIN

<400> SEQUENCE: 38

Leu Lys Leu Leu Asp Asn Trp Asp Ser Val Thr Ser Thr Phe Ser Cys
1               5                   10                  15

Leu Arg

<210> SEQ ID NO 39
<211> LENGTH: 30
<212> TYPE: PRT
<213> ORGANISM: ARTIFICIAL SEQUENCE
<220> FEATURE:
<221> NAME/KEY: PEPTIDE
<222> LOCATION: (1)..(18)
<223> OTHER INFORMATION: HUMAN GENETIC ORIGIN

<400> SEQUENCE: 39

Pro Ala Leu Glu Asp Leu Arg Gln Gly Leu Leu Pro Leu Lys Leu Cys
1               5                   10                  15

Asp Asn Trp Asp Ser Val Thr Ser Thr Phe Ser Lys Leu Arg
            20                  25                  30

<210> SEQ ID NO 40
<211> LENGTH: 30
<212> TYPE: PRT
<213> ORGANISM: ARTIFICIAL SEQUENCE
<220> FEATURE:
<221> NAME/KEY: PEPTIDE
<222> LOCATION: (1)..(30)
<223> OTHER INFORMATION: HUMAN GENETIC ORIGIN

<400> SEQUENCE: 40

Pro Ala Leu Glu Asp Leu Arg Gln Gly Leu Leu Pro Leu Lys Leu Leu
1               5                   10                  15

Asp Asn Trp Asp Ser Val Thr Ser Thr Phe Ser Lys Leu Arg
            20                  25                  30

<210> SEQ ID NO 41
<211> LENGTH: 30
<212> TYPE: PRT
<213> ORGANISM: ARTIFICIAL SEQUENCE
<220> FEATURE:
<221> NAME/KEY: PEPTIDE
<222> LOCATION: (1)..(30)
<223> OTHER INFORMATION: HUMAN GENETIC ORIGIN

<400> SEQUENCE: 41

Pro Ala Leu Glu Asp Leu Cys Gln Gly Leu Leu Pro Leu Lys Leu Leu
1               5                   10                  15

Asp Asn Trp Asp Ser Val Thr Ser Thr Phe Ser Lys Leu Arg
            20                  25                  30
```

<210> SEQ ID NO 42
<211> LENGTH: 30
<212> TYPE: PRT
<213> ORGANISM: ARTIFICIAL SEQUENCE
<220> FEATURE:
<221> NAME/KEY: PEPTIDE
<222> LOCATION: (1)..(30)
<223> OTHER INFORMATION: HUMAN GENETIC ORIGIN

<400> SEQUENCE: 42

Pro Ala Leu Glu Asp Leu Arg Gln Gly Leu Leu Pro Leu Cys Leu Leu
1               5                   10                  15

Asp Asn Trp Asp Ser Val Thr Ser Thr Phe Ser Lys Leu Arg
            20                  25                  30

<210> SEQ ID NO 43
<211> LENGTH: 30
<212> TYPE: PRT
<213> ORGANISM: ARTIFICIAL SEQUENCE
<220> FEATURE:
<221> NAME/KEY: PEPTIDE
<222> LOCATION: (1)..(30)
<223> OTHER INFORMATION: HUMAN GENETIC ORIGIN

<400> SEQUENCE: 43

Pro Ala Leu Glu Asp Leu Arg Gln Gly Leu Leu Pro Leu Lys Cys Leu
1               5                   10                  15

Asp Asn Trp Asp Ser Val Thr Ser Thr Phe Ser Lys Leu Arg
            20                  25                  30

<210> SEQ ID NO 44
<211> LENGTH: 30
<212> TYPE: PRT
<213> ORGANISM: ARTIFICIAL SEQUENCE
<220> FEATURE:
<221> NAME/KEY: PEPTIDE
<222> LOCATION: (1)..(30)
<223> OTHER INFORMATION: HUMAN GENETIC ORIGIN

<400> SEQUENCE: 44

Pro Ala Leu Glu Asp Leu Arg Gln Gly Leu Leu Pro Leu Lys Leu Leu
1               5                   10                  15

Cys Asn Trp Asp Ser Val Thr Ser Thr Phe Ser Lys Leu Arg
            20                  25                  30

<210> SEQ ID NO 45
<211> LENGTH: 30
<212> TYPE: PRT
<213> ORGANISM: ARTIFICIAL SEQUENCE
<220> FEATURE:
<221> NAME/KEY: PEPTIDE
<222> LOCATION: (1)..(30)
<223> OTHER INFORMATION: HUMAN GENETIC ORIGIN

<400> SEQUENCE: 45

Pro Ala Leu Glu Asp Leu Arg Gln Gly Leu Leu Pro Leu Lys Leu Leu
1               5                   10                  15

Asp Cys Trp Asp Ser Val Thr Ser Thr Phe Ser Lys Leu Arg
            20                  25                  30

<210> SEQ ID NO 46
<211> LENGTH: 30
<212> TYPE: PRT
<213> ORGANISM: ARTIFICIAL SEQUENCE
<220> FEATURE:
<221> NAME/KEY: PEPTIDE
<222> LOCATION: (1)..(30)

<223> OTHER INFORMATION: HUMAN GENETIC ORIGIN

<400> SEQUENCE: 46

Pro Ala Leu Glu Asp Leu Arg Gln Gly Leu Leu Pro Leu Lys Leu Leu
1               5                   10                  15

Asp Asn Trp Asp Ser Val Thr Ser Thr Phe Ser Cys Leu Arg
            20                  25                  30

<210> SEQ ID NO 47
<211> LENGTH: 18
<212> TYPE: PRT
<213> ORGANISM: ARTIFICIAL SEQUENCE
<220> FEATURE:
<221> NAME/KEY: PEPTIDE
<222> LOCATION: (1)..(18)
<223> OTHER INFORMATION: HUMAN GENETIC ORIGIN

<400> SEQUENCE: 47

Gly Ala Asp Met Glu Asp Val Cys Gly Arg Leu Val Gln Tyr Arg Gly
1               5                   10                  15

Glu Val

<210> SEQ ID NO 48
<211> LENGTH: 18
<212> TYPE: PRT
<213> ORGANISM: ARTIFICIAL SEQUENCE
<220> FEATURE:
<221> NAME/KEY: PEPTIDE
<222> LOCATION: (1)..(18)
<223> OTHER INFORMATION: HUMAN GENETIC ORIGIN

<400> SEQUENCE: 48

Gly Ala Asp Met Glu Asp Val Arg Gly Arg Leu Val Gln Tyr Arg Gly
1               5                   10                  15

Glu Val

<210> SEQ ID NO 49
<211> LENGTH: 18
<212> TYPE: PRT
<213> ORGANISM: ARTIFICIAL SEQUENCE
<220> FEATURE:
<221> NAME/KEY: PEPTIDE
<222> LOCATION: (1)..(18)
<223> OTHER INFORMATION: HUMAN GENETIC ORIGIN

<400> SEQUENCE: 49

Gly Ala Asp Met Glu Asp Cys Arg Gly Arg Leu Val Gln Tyr Arg Gly
1               5                   10                  15

Glu Val

<210> SEQ ID NO 50
<211> LENGTH: 18
<212> TYPE: PRT
<213> ORGANISM: ARTIFICIAL SEQUENCE
<220> FEATURE:
<221> NAME/KEY: PEPTIDE
<222> LOCATION: (1)..(18)
<223> OTHER INFORMATION: HUMAN GENETIC ORIGIN

<400> SEQUENCE: 50

Gly Ala Asp Met Glu Asp Val Arg Cys Arg Leu Val Gln Tyr Arg Gly
1               5                   10                  15

Glu Val

```
<210> SEQ ID NO 51
<211> LENGTH: 18
<212> TYPE: PRT
<213> ORGANISM: ARTIFICIAL SEQUENCE
<220> FEATURE:
<221> NAME/KEY: PEPTIDE
<222> LOCATION: (1)..(18)
<223> OTHER INFORMATION: HUMAN GENETIC ORIGIN

<400> SEQUENCE: 51

Gly Ala Asp Met Glu Asp Val Arg Gly Cys Leu Val Gln Tyr Arg Gly
1               5                   10                  15

Glu Val

<210> SEQ ID NO 52
<211> LENGTH: 18
<212> TYPE: PRT
<213> ORGANISM: ARTIFICIAL SEQUENCE
<220> FEATURE:
<221> NAME/KEY: PEPTIDE
<222> LOCATION: (1)..(18)
<223> OTHER INFORMATION: HUMAN GENETIC ORIGIN

<400> SEQUENCE: 52

Ala Arg Leu Ser Arg Cys Val Gln Val Leu Ser Arg Lys Leu Thr Leu
1               5                   10                  15

Lys Ala

<210> SEQ ID NO 53
<211> LENGTH: 18
<212> TYPE: PRT
<213> ORGANISM: ARTIFICIAL SEQUENCE
<220> FEATURE:
<221> NAME/KEY: PEPTIDE
<222> LOCATION: (1)..(18)
<223> OTHER INFORMATION: HUMAN GENETIC ORIGIN

<400> SEQUENCE: 53

Ala Arg Leu Ser Arg Gly Val Gln Val Leu Ser Arg Lys Leu Thr Leu
1               5                   10                  15

Lys Ala

<210> SEQ ID NO 54
<211> LENGTH: 18
<212> TYPE: PRT
<213> ORGANISM: ARTIFICIAL SEQUENCE
<220> FEATURE:
<221> NAME/KEY: PEPTIDE
<222> LOCATION: (1)..(18)
<223> OTHER INFORMATION: HUMAN GENETIC ORIGIN

<400> SEQUENCE: 54

Ala Arg Leu Cys Arg Gly Val Gln Val Leu Ser Arg Lys Leu Thr Leu
1               5                   10                  15

Lys Ala

<210> SEQ ID NO 55
<211> LENGTH: 18
<212> TYPE: PRT
<213> ORGANISM: ARTIFICIAL SEQUENCE
<220> FEATURE:
<221> NAME/KEY: PEPTIDE
<222> LOCATION: (1)..(18)
<223> OTHER INFORMATION: HUMAN GENETIC ORIGIN

<400> SEQUENCE: 55
```

Ala Arg Leu Ser Cys Gly Val Gln Val Leu Ser Arg Lys Leu Thr Leu
1               5                   10                  15

Lys Ala

<210> SEQ ID NO 56
<211> LENGTH: 18
<212> TYPE: PRT
<213> ORGANISM: ARTIFICIAL SEQUENCE
<220> FEATURE:
<221> NAME/KEY: PEPTIDE
<222> LOCATION: (1)..(18)
<223> OTHER INFORMATION: HUMAN GENETIC ORIGIN

<400> SEQUENCE: 56

Ala Arg Leu Ser Arg Gly Cys Gln Val Leu Ser Arg Lys Leu Thr Leu
1               5                   10                  15

Lys Ala

<210> SEQ ID NO 57
<211> LENGTH: 18
<212> TYPE: PRT
<213> ORGANISM: ARTIFICIAL SEQUENCE
<220> FEATURE:
<221> NAME/KEY: PEPTIDE
<222> LOCATION: (1)..(18)
<223> OTHER INFORMATION: HUMAN GENETIC ORIGIN

<400> SEQUENCE: 57

Ala Arg Leu Ser Arg Gly Val Gln Val Leu Ser Arg Lys Cys Thr Leu
1               5                   10                  15

Lys Ala

<210> SEQ ID NO 58
<211> LENGTH: 36
<212> TYPE: PRT
<213> ORGANISM: ARTIFICIAL SEQUENCE
<220> FEATURE:
<221> NAME/KEY: PEPTIDE
<222> LOCATION: (1)..(36)
<223> OTHER INFORMATION: HUMAN GENETIC ORIGIN

<400> SEQUENCE: 58

Ala Arg Leu Ser Arg Cys Val Gln Val Leu Ser Arg Lys Leu Thr Leu
1               5                   10                  15

Lys Ala Lys Ala Leu His Ala Arg Ile Gln Gln Asn Leu Asp Gln Leu
                20                  25                  30

Arg Glu Glu Leu
            35

<210> SEQ ID NO 59
<211> LENGTH: 36
<212> TYPE: PRT
<213> ORGANISM: ARTIFICIAL SEQUENCE
<220> FEATURE:
<221> NAME/KEY: PEPTIDE
<222> LOCATION: (1)..(36)
<223> OTHER INFORMATION: HUMAN GENETIC ORIGIN

<400> SEQUENCE: 59

Ala Arg Leu Ser Arg Gly Val Gln Val Leu Ser Arg Lys Leu Thr Leu
1               5                   10                  15

Lys Ala Lys Ala Leu His Ala Arg Ile Gln Gln Asn Leu Asp Gln Leu
                20                  25                  30

Arg Glu Glu Leu

```
<210> SEQ ID NO 60
<211> LENGTH: 36
<212> TYPE: PRT
<213> ORGANISM: ARTIFICIAL SEQUENCE
<220> FEATURE:
<221> NAME/KEY: PEPTIDE
<222> LOCATION: (1)..(36)
<223> OTHER INFORMATION: HUMAN GENETIC ORIGIN

<400> SEQUENCE: 60

Ala Arg Leu Cys Arg Gly Val Gln Val Leu Ser Arg Lys Leu Thr Leu
 1               5                  10                  15

Lys Ala Lys Ala Leu His Ala Arg Ile Gln Gln Asn Leu Asp Gln Leu
            20                  25                  30

Arg Glu Glu Leu
        35

<210> SEQ ID NO 61
<211> LENGTH: 36
<212> TYPE: PRT
<213> ORGANISM: ARTIFICIAL SEQUENCE
<220> FEATURE:
<221> NAME/KEY: PEPTIDE
<222> LOCATION: (1)..(36)
<223> OTHER INFORMATION: HUMAN GENETIC ORIGIN

<400> SEQUENCE: 61

Ala Arg Leu Ser Cys Gly Val Gln Val Leu Ser Arg Lys Leu Thr Leu
 1               5                  10                  15

Lys Ala Lys Ala Leu His Ala Arg Ile Gln Gln Asn Leu Asp Gln Leu
            20                  25                  30

Arg Glu Glu Leu
        35

<210> SEQ ID NO 62
<211> LENGTH: 36
<212> TYPE: PRT
<213> ORGANISM: ARTIFICIAL SEQUENCE
<220> FEATURE:
<221> NAME/KEY: PEPTIDE
<222> LOCATION: (1)..(36)
<223> OTHER INFORMATION: HUMAN GENETIC ORIGIN

<400> SEQUENCE: 62

Ala Arg Leu Ser Arg Gly Cys Gln Val Leu Ser Arg Lys Leu Thr Leu
 1               5                  10                  15

Lys Ala Lys Ala Leu His Ala Arg Ile Gln Gln Asn Leu Asp Gln Leu
            20                  25                  30

Arg Glu Glu Leu
        35

<210> SEQ ID NO 63
<211> LENGTH: 36
<212> TYPE: PRT
<213> ORGANISM: ARTIFICIAL SEQUENCE
<220> FEATURE:
<221> NAME/KEY: PEPTIDE
<222> LOCATION: (1)..(36)
<223> OTHER INFORMATION: HUMAN GENETIC ORIGIN

<400> SEQUENCE: 63

Ala Arg Leu Ser Arg Gly Val Gln Val Leu Ser Arg Lys Cys Thr Leu
 1               5                  10                  15
```

```
Lys Ala Lys Ala Leu His Ala Arg Ile Gln Gln Asn Leu Asp Gln Leu
            20                  25                  30

Arg Glu Glu Leu
        35

<210> SEQ ID NO 64
<211> LENGTH: 22
<212> TYPE: PRT
<213> ORGANISM: ARTIFICIAL SEQUENCE
<220> FEATURE:
<221> NAME/KEY: PEPTIDE
<222> LOCATION: (1)..(22)
<223> OTHER INFORMATION: HUMAN GENETIC ORIGIN

<400> SEQUENCE: 64

Ala Thr Leu Lys Asp Ser Leu Cys Gln Asp Leu Asn Asn Met Asn Lys
1               5                   10                  15

Phe Leu Glu Lys Leu Arg
            20

<210> SEQ ID NO 65
<211> LENGTH: 22
<212> TYPE: PRT
<213> ORGANISM: ARTIFICIAL SEQUENCE
<220> FEATURE:
<221> NAME/KEY: PEPTIDE
<222> LOCATION: (1)..(22)
<223> OTHER INFORMATION: HUMAN GENETIC ORIGIN

<400> SEQUENCE: 65

Ala Thr Leu Lys Asp Ser Leu Glu Gln Asp Leu Asn Asn Met Asn Lys
1               5                   10                  15

Phe Leu Glu Lys Leu Arg
            20

<210> SEQ ID NO 66
<211> LENGTH: 22
<212> TYPE: PRT
<213> ORGANISM: ARTIFICIAL SEQUENCE
<220> FEATURE:
<221> NAME/KEY: PEPTIDE
<222> LOCATION: (1)..(22)
<223> OTHER INFORMATION: HUMAN GENETIC ORIGIN

<400> SEQUENCE: 66

Ala Thr Leu Cys Asp Ser Leu Glu Gln Asp Leu Asn Asn Met Asn Lys
1               5                   10                  15

Phe Leu Glu Lys Leu Arg
            20

<210> SEQ ID NO 67
<211> LENGTH: 22
<212> TYPE: PRT
<213> ORGANISM: ARTIFICIAL SEQUENCE
<220> FEATURE:
<221> NAME/KEY: PEPTIDE
<222> LOCATION: (1)..(22)
<223> OTHER INFORMATION: HUMAN GENETIC ORIGIN

<400> SEQUENCE: 67

Ala Thr Leu Lys Asp Cys Leu Glu Gln Asp Leu Asn Asn Met Asn Lys
1               5                   10                  15

Phe Leu Glu Lys Leu Arg
            20
```

<210> SEQ ID NO 68
<211> LENGTH: 22
<212> TYPE: PRT
<213> ORGANISM: ARTIFICIAL SEQUENCE
<220> FEATURE:
<221> NAME/KEY: PEPTIDE
<222> LOCATION: (1)..(22)
<223> OTHER INFORMATION: HUMAN GENETIC ORIGIN

<400> SEQUENCE: 68

Ala Thr Leu Lys Asp Ser Cys Glu Gln Asp Leu Asn Asn Met Asn Lys
1               5                   10                  15

Phe Leu Glu Lys Leu Arg
            20

<210> SEQ ID NO 69
<211> LENGTH: 22
<212> TYPE: PRT
<213> ORGANISM: ARTIFICIAL SEQUENCE
<220> FEATURE:
<221> NAME/KEY: PEPTIDE
<222> LOCATION: (1)..(22)
<223> OTHER INFORMATION: HUMAN GENETIC ORIGIN

<400> SEQUENCE: 69

Ala Thr Leu Lys Asp Ser Leu Glu Cys Asp Leu Asn Asn Met Asn Lys
1               5                   10                  15

Phe Leu Glu Lys Leu Arg
            20

<210> SEQ ID NO 70
<211> LENGTH: 22
<212> TYPE: PRT
<213> ORGANISM: ARTIFICIAL SEQUENCE
<220> FEATURE:
<221> NAME/KEY: PEPTIDE
<222> LOCATION: (1)..(22)
<223> OTHER INFORMATION: HUMAN GENETIC ORIGIN

<400> SEQUENCE: 70

Ala Thr Leu Lys Asp Ser Leu Glu Gln Cys Leu Asn Asn Met Asn Lys
1               5                   10                  15

Phe Leu Glu Lys Leu Arg
            20

<210> SEQ ID NO 71
<211> LENGTH: 11
<212> TYPE: PRT
<213> ORGANISM: ARTIFICIAL SEQUENCE
<220> FEATURE:
<221> NAME/KEY: PEPTIDE
<222> LOCATION: (1)..(11)
<223> OTHER INFORMATION: HUMAN GENETIC ORIGIN

<400> SEQUENCE: 71

Glu Thr Gly Asp Leu Trp Val Gly Cys His Pro
1               5                   10

<210> SEQ ID NO 72
<211> LENGTH: 23
<212> TYPE: PRT
<213> ORGANISM: ARTIFICIAL SEQUENCE
<220> FEATURE:
<221> NAME/KEY: PEPTIDE
<222> LOCATION: (1)..(23)
<223> OTHER INFORMATION: HUMAN GENETIC ORIGIN

```
<400> SEQUENCE: 72

Glu Thr Gly Asp Leu Trp Val Gly Cys His Pro Asn Gly Met Lys Ile
1               5                   10                  15

Phe Phe Tyr Asp Ser Glu Asn
            20

<210> SEQ ID NO 73
<211> LENGTH: 40
<212> TYPE: PRT
<213> ORGANISM: ARTIFICIAL SEQUENCE
<220> FEATURE:
<221> NAME/KEY: PEPTIDE
<222> LOCATION: (1)..(40)
<223> OTHER INFORMATION: HUMAN GENETIC ORIGIN

<400> SEQUENCE: 73

Leu Lys Ser Leu Asp Phe Asn Thr Leu Val Asp Asn Ile Ser Val Asp
1               5                   10                  15

Pro Glu Thr Gly Asp Leu Trp Val Gly Cys His Pro Asn Gly Met Lys
            20                  25                  30

Ile Phe Phe Tyr Asp Ser Glu Asn
        35                  40

<210> SEQ ID NO 74
<211> LENGTH: 18
<212> TYPE: PRT
<213> ORGANISM: ARTIFICIAL SEQUENCE
<220> FEATURE:
<221> NAME/KEY: PEPTIDE
<222> LOCATION: (1)..(18)
<223> OTHER INFORMATION: SYNTHETIC SEQUENCE

<400> SEQUENCE: 74

Asp Trp Leu Cys Ala Phe Tyr Asp Lys Val Ala Glu Lys Leu Lys Glu
1               5                   10                  15

Ala Phe

<210> SEQ ID NO 75
<211> LENGTH: 18
<212> TYPE: PRT
<213> ORGANISM: ARTIFICIAL SEQUENCE
<220> FEATURE:
<221> NAME/KEY: PEPTIDE
<222> LOCATION: (1)..(18)
<223> OTHER INFORMATION: SYNTHETIC SEQUENCE

<400> SEQUENCE: 75

Asp Trp Leu Lys Ala Phe Tyr Asp Lys Val Ala Glu Lys Leu Lys Glu
1               5                   10                  15

Ala Phe

<210> SEQ ID NO 76
<211> LENGTH: 18
<212> TYPE: PRT
<213> ORGANISM: ARTIFICIAL SEQUENCE
<220> FEATURE:
<221> NAME/KEY: PEPTIDE
<222> LOCATION: (1)..(18)
<223> OTHER INFORMATION: SYNTHETIC SEQUENCE

<400> SEQUENCE: 76

Asp Cys Leu Lys Ala Phe Tyr Asp Lys Val Ala Glu Lys Leu Lys Glu
1               5                   10                  15

Ala Phe
```

<210> SEQ ID NO 77
<211> LENGTH: 18
<212> TYPE: PRT
<213> ORGANISM: ARTIFICIAL SEQUENCE
<220> FEATURE:
<221> NAME/KEY: PEPTIDE
<222> LOCATION: (1)..(18)
<223> OTHER INFORMATION: SYNTHETIC SEQUENCE

<400> SEQUENCE: 77

Asp Trp Cys Lys Ala Phe Tyr Asp Lys Val Ala Glu Lys Leu Lys Glu
1               5                   10                  15

Ala Phe

<210> SEQ ID NO 78
<211> LENGTH: 18
<212> TYPE: PRT
<213> ORGANISM: ARTIFICIAL SEQUENCE
<220> FEATURE:
<221> NAME/KEY: PEPTIDE
<222> LOCATION: (1)..(18)
<223> OTHER INFORMATION: SYNTHETIC SEQUENCE

<400> SEQUENCE: 78

Asp Trp Leu Lys Cys Phe Tyr Asp Lys Val Ala Glu Lys Leu Lys Glu
1               5                   10                  15

Ala Phe

<210> SEQ ID NO 79
<211> LENGTH: 18
<212> TYPE: PRT
<213> ORGANISM: ARTIFICIAL SEQUENCE
<220> FEATURE:
<221> NAME/KEY: PEPTIDE
<222> LOCATION: (1)..(18)
<223> OTHER INFORMATION: SYNTHETIC SEQUENCE

<400> SEQUENCE: 79

Asp Trp Leu Lys Ala Cys Tyr Asp Lys Val Ala Glu Lys Leu Lys Glu
1               5                   10                  15

Ala Phe

<210> SEQ ID NO 80
<211> LENGTH: 18
<212> TYPE: PRT
<213> ORGANISM: ARTIFICIAL SEQUENCE
<220> FEATURE:
<221> NAME/KEY: PEPTIDE
<222> LOCATION: (1)..(18)
<223> OTHER INFORMATION: SYNTHETIC SEQUENCE

<400> SEQUENCE: 80

Asp Trp Leu Lys Ala Phe Tyr Asp Lys Cys Ala Glu Lys Leu Lys Glu
1               5                   10                  15

Ala Phe

<210> SEQ ID NO 81
<211> LENGTH: 18
<212> TYPE: PRT
<213> ORGANISM: ARTIFICIAL SEQUENCE
<220> FEATURE:
<221> NAME/KEY: PEPTIDE
<222> LOCATION: (1)..(18)
<223> OTHER INFORMATION: SYNTHETIC SEQUENCE

```
<400> SEQUENCE: 81

Asp Trp Leu Lys Ala Phe Tyr Asp Lys Val Cys Glu Lys Leu Lys Glu
1               5                   10                  15

Ala Phe

<210> SEQ ID NO 82
<211> LENGTH: 37
<212> TYPE: PRT
<213> ORGANISM: ARTIFICIAL SEQUENCE
<220> FEATURE:
<221> NAME/KEY: PEPTIDE
<222> LOCATION: (1)..(37)
<223> OTHER INFORMATION: SYNTHETIC SEQUENCE

<400> SEQUENCE: 82

Leu Glu Lys Leu Asn Ser Cys Leu Arg Asp Arg Leu Ser Ala Leu Thr
1               5                   10                  15

Asp Thr Pro Leu Glu Glu Leu Arg Asp Ser Leu Arg Ser Arg Leu Asp
            20                  25                  30

Ala Leu Arg Ser Thr
        35

<210> SEQ ID NO 83
<211> LENGTH: 18
<212> TYPE: PRT
<213> ORGANISM: ARTIFICIAL SEQUENCE
<220> FEATURE:
<221> NAME/KEY: PEPTIDE
<222> LOCATION: (1)..(18)
<223> OTHER INFORMATION: SYNTHETIC SEQUENCE

<400> SEQUENCE: 83

Leu Glu Lys Leu Asn Ser Cys Leu Arg Asp Arg Leu Ser Ala Leu Thr
1               5                   10                  15

Asp Thr

<210> SEQ ID NO 84
<211> LENGTH: 18
<212> TYPE: PRT
<213> ORGANISM: ARTIFICIAL SEQUENCE
<220> FEATURE:
<221> NAME/KEY: PEPTIDE
<222> LOCATION: (1)..(18)
<223> OTHER INFORMATION: SYNTHETIC SEQUENCE

<400> SEQUENCE: 84

Leu Glu Glu Leu Arg Asp Ser Leu Arg Ser Arg Leu Asp Ala Leu Arg
1               5                   10                  15

Ser Thr
```

CYSTEINE-CONTAINING PEPTIDES HAVING ANTIOXIDANT PROPERTIES

CROSS-REFERENCE TO PRIOR APPLICATION

This application claims priority to application Ser. No. 60/289,944, which was filed on May 9, 2001, the contents of which are incorporated in its entirety.

STATEMENT OF GOVERNMENT SUPPORT

This invention was made during work partially supported by the U.S. Department of Energy under Contract No. DE-AC03-76SF00098. This work was also supported by NIH grant HL59483. The government has certain rights in this invention.

BACKGROUND OF THE INVENTION

1. Field of the Invention

This invention generally relates to human lipid metabolism, particularly to HDL-related proteins, their mutations, and peptides designed based on these mutations which have antioxidant properties beneficial in the regulation of cardiovascular disease (CVD), bone diseases and other inflammatory related diseases.

2. Description of the Related Art

Cardiovascular disease (CVD) is the number one cause of death in Western societies and its prevalence is increasing worldwide. One of the strongest predictors of risk is the plasma concentration of high density lipoprotein (HDL) which exhibits an inverse relationship to the risk (Gordon, T., et al., Am. J. Med. 62:707–714, 1997; Wilson, P. W. F., Am. J. Cardiol. 66:7A10A, 1990). Despite the strong epidemiological data relating increased plasma HDL to protection against CVD, a number of rare inheritable traits have been described which result in low plasma HDL concentrations but no increase in CVD. These inheritable traits are, in part, attributed to mutations in apolipoproteinA-I, the major protein component of HDL (Assmann, G., et al, Circulation 87:[suppl III]:III-28-III-34, 1993).

ApolipoproteinA-$I_{Milano}$ and apoA-$I_{Paris}$ are examples of natural variants of apoA-I that manifest HDL deficiencies but there is no apparent CVD in affected subjects. See Weisgraber, K. H., et al., J. Clin. Invest. 66:901–907, 1980; Franceschini, G., et al., i J. Clin. Invest. 66:892–900, 1980; Bruckert, E., et al., Atherosclerosis, 128:121–128, 1997. Indeed, a recent clinical study showed that carriers of apoA-$I_{Milano}$ exhibited normal intimal thickness of carotid arteries compared to age- and sex-matched controls; whereas, hypoalphalipoproteinemic individuals showed intimal thickening as judged by B-mode ultrasound (Sitori, C. R., et al., Circulation 103:1949–1954, 2001). Studies utilizing mice and rabbits support clinical studies by demonstrating that injection of recombinant apoA-$I_{Milano}$ protects against atherosclerosis (Shah, P. K., et al., Circulation 97:780–785, 1998; Shah, P. K., et al., Circulation 103: 3047–3050, 2001; Ameli, S., et al., Circulation 90:1935–1941, 1994). However, the mechanism(s) by which apoA-$I_{Milano}$ and apoA-$I_{Paris}$ exert anti-atherogenic effects are not completely understood.

All known human carriers of apoA-$I_{Milano}$ and apoA-$I_{Paris}$ are heterozygous for R173C and R151C mutations in apoA-I primary sequence, respectively (Weisgraber, K. H., et al., J. Clin. Invest. 66:901–907, 1980; Bruckert, E., et al., Atherosclerosis, 128:121–128, 1997). The introduction of a cysteine residue in a normally cysteine-free apolipoprotein allows for the formation of homodimers and heterodimers with apoA-II. Dimerization of the cysteine variants inhibits HDL maturation via mechanisms related, in part, to impaired activation of lecithin: cholesterol acyltransferase, the enzyme that catalyzes cholesterol esterification on HDL (Franceschini, G., et al., J. Biol Chem. 265:12224–12231, 1990; Calabresi, L., et al., Biochem. Biophys. Res. Comm. 232:345–349, 1997; Daum, U., et al., J. Mol. Med. 77:614–622, 1999). ApoA-$I_{Milano}$ apoA-$I_{Paris}$ are rapidly cleared from the plasma compartment in humans thus contributing to the HDL deficiency in vivo (Roma P, et al., J. Clin. Invest. 91:1445–1452, 1993; Perez-Mendez, O., et al., Atherosclerosis 148:317–326, 2000). However, the fractional catabolic rate of apoA-$I_{Paris}$ appears to be different from that of apoA-$I_{Milano}$ suggesting that the two cysteine variants may differ in their metabolic behavior. Human carriers of apoA-$I_{Milano}$ and apoA-$I_{Paris}$ also exhibit mild hypertriglyceridemia in addition to the HDL deficiency (Bruckert, E., et al., Atherosclerosis, 128:121–128, 1997; Franceschini G., et al., Atherosclerosis 7:426–435, 1987).

The C-terminal lipid-binding domain of Apo A-$I_{WT}$ consists of a series of helical repeats separated by proline residues. The amphipathic alpha helix 7 containing R173C is flanked by two amphipathic alpha helices of relatively greater lipid binding affinity. The lipid binding affinity of the helical repeats alternate, but the two end helices of Apo A-I exhibit the highest lipid-binding affinity (Palgunachari, M.N., et al., Arterioscier. Thromb. Vasc. Biol. 16:328–338, 1996). The relatively low lipid-binding affinity associated with helix 7, where R173C is located, may allow a high degree of movement of this particular helix on phospholipid surfaces thus maximizing the freQuency of collision between the free thiol at position 173 with reactive lipid peroxides. Increased flexibility of helix 7, which is located in the central region of the C-terminal lipid-binding domain, may be optimized in the presence of deoxycholate used in the preparation of the phospholipid micelles.

The paradox of abnormal lipoprotein metabolism and protection from CVD has led to the suggestion that the cysteine substitution for arginine in the lipid-binding domain of apoA-I may impart a gain-of-function protecting against atherosclerosis. As thiol groups in proteins are strong nucleophiles often participating in electron transfer reactions, we hypothesized that the monomeric forms of apoA-$I_{Milano}$ and apoA-$I_{Paris}$ which contain a free thiol, may possess an antioxidant activity distinct from that of apoA-$I_{WT}$.

Individuals with these substitutions are known to have low levels of the "good" cholesterol HDL, but yet do not suffer from significantly increased levels of CVD. Oda et al. disclose cysteine substitutions in Apolipoprotein A-I in Biochemistry 40 (2001) 1710–1718 other substitutions are disclosed at Atherosclerosis 128 (1997) 121–128 ; Atherosclerosis 135 (1997) 181–185. Antioxidant action of HDL is discussed at Atherosclerosis 135 (1997) 193–204.

These cysteine for arginine substitutions in the Apo A-I variant is of special interest in treatment of cardiovascular disease. The dimer of Apolipoprotein apoA-$I_{Milano}$ and the process of producing and purifying the dimer composition have been disclosed by Sirtori et al, in U.S. Pat. No. 5,876,968, which is hereby incorporated by reference. The process described by Sirtori et al. relies on converting any monomer present to a substantially pure form of the dimer form of apoA-$I_{Milano}$ of at least 90% purity.

Segrest et al., in U.S. Pat. No. 4,643,988, discloses amphipathic peptides that are useful for treatment and prevention of athersclerosis. The Segrest peptides, generally referred to as 18A and 18pA, are based on an idealistic model of an amphipathic alpha helix that possesses a primary amino acid sequence distinct from that of apoA-I. However, the peptides form Class A amphipathic alpha helices with positively charged amino acids at the interface of polar/nonpolar region and negatively charged residues located in the middle of the polar face of the helix.

Segrest et. al. described the use and properties of 18A and 18pA; the latter representing a series of two 18A peptides linked by a proline residue. The sequence of 18A is as follows: DWLKAFYDKVAEKLKEAF (SEQ ID NO:75). Various conservative substitutions (for example positively charged lysine residues in place of positively charged argine residues) that ndo not change the overall design of the class A amphipathic alpha helix are also claimed. Additional substitutins of D- for L- amino acid isoforms are described as well as replacement of naturally ocurring amino acids for synthethic derivatives (i.e. substitutions of alanine for alapha-naphthylalanine). While an amphipathic peptide is disclosed, the peptide does not possess a cysteine residue and thus lacks the antioxidant activity shown to be possessed by apoA-I$_{Milano}$.

Garber et al., disclose on U.S. Pat. No. 6,156,727, anti-atherosclerotic peptides and a transgenic mouse model of atherosclerosis. Garber et al. utilize the same peptides as described above by Segrest et al., however Garber et al. created transgenic mice that express the peptides 18A and 37pA, the latter sometimes is referred to as 18A-Pro-18A. Again, these peptide does not possess a cysteine residue and thus lack the antioxidant activity shown to be possessed by apoA-I$_{Milano}$.

Lees et al., disclose in U.S. Pat. No. 5,955,055, synthetic peptides for arterial imaging at vascular imaging sites, that mimic apolipoprotein B (apoB), apolipoprotein A-I or elastin proteins and is hereby incorporated by reference in its entirety. The Lees peptides are derived (mostly) from apoB and elastin/collagen and are not similar to the peptides we now disclose. The following sequence is used as is based on apoB: YRALVDTLKFVTQAEGAL (SEQ ID NO:89). The sequence derived from apoA-I described by Lees et al. is: YVLDEFREKLNEELEALKQ (SEQ ID NO:90). There is no exact sequence match to apoA-I, probably because of conservative substitutions, and the peptide is not at all similar to any of the peptides we now disclose.

Moreover, none of the peptides in the above mentioned patents are based on Apolipoprotein E3 (apoE3) and Apolipoprotein A-V (apoAV). This is because the mechanisms responsible for the antioxidant properties of apoE3 have not been fully defined until now. ApoAV is a new apolipoprotein that has recently been described and very little is known about its function. Thus, peptides based on apoAV provide new avenues for development of therapeutic agents. It is also clear from our studies that the antioxidant properties of apoA-I$_{Milano}$ and its peptide mimetics are specifically directed toward phospholipid surfaces which none of these above-mentioned patented peptides are shown to be directed toward.

BRIEF SUMMARY OF THE INVENTION

The present invention describes a new series of diagnostic and therapeutic peptides that possess a novel antioxidant activity, such as has been associated with the monomeric forms of apoA-I$_{Milano}$ and apoA-I$_{Paris}$ proteins. A critical feature of the present peptides is the placement of a cysteine residue at the polar/nonpolar interface of an amphipathic alpha helix just as in the apoA-I$_{Milano}$ and apoA-I$_{Paris}$ cysteine variants. The presence of a cysteine residue at the polar/nonploar interface of the synthetic peptides confers a potent antioxidant activity that is directed toward lipid surfaces effectively blocking oxidation of phospholipid. The water accessibility of the free cysteine residue enables potential interaction with water-soluble antioxidants such as reduced glutathione thereby enhancing the overall capacity of the peptides to inhibit phospholipid oxidation. This indicates that the peptides may be used in combination with other safe and effective therapies to promote beneficial interactions for long-term protection against inflammatory related events.

Structural analyses revealed identical placement of a cysteine residue at the polar/nonpolar interface of an amphipathic alpha helix within apoE3 thus defining the mechanism for the antioxidant activity of apoE3. A similar "motif" in apoAV is also used to create new peptides.

In the present peptides have also been developed in which the position of the cysteine residue is changed around the face of the amphipathic alpha helix. Such changes in placement of the cysteine residue is predicted to specifically alter the functionality of the peptides in a systematic fashion. For example, the cysteine residue is placed in the middle of the nonploar face of the amphipathic alpha helix to inhibit specific interaction with water-soluble antioxidants such as reduced glutathione. This enables the development of important biological tools to determine whether such interactions are important in protecting against disease thus allowing the identification of new drug targets and providing a basis for rationale drug design. This has led to the creation of a generic amphipathic alpha helix for the development of tailor-made pharmacteuticals of defined functionality including specific antioxidant activity attributed to strategic cysteine placement, LCAT activation properties endowed via arginine clustering at the polar/nonpolar interface, and cholesterol efflux properties obtained by either phenylalanine placement or by combining unique helical segments.

The present invention comprises peptides possessing antioxidant activity and which may be derived from naturally occurring HDL -associated proteins or may be designed de novo according to the principles outlined herein. The peptides of the present invention may be characterized as follows, where the conventional single letter amino acid code letters are used:

| | | |
|---|---|---|
| SDELRQCLAARLEALKEN | 167-R173C-184 | SEQ ID NO: 1 |
| SDEL<u>RQR</u>L<u>A</u>ARLE<u>A</u>LKEN | Control wild type 167–184 | SEQ ID NO: 2 |
| SDELCQRLAARLEALKEN | 167-R171C-184 | SEQ ID NO: 3 |
| SDELRCRLAARLEALKEN | 167-Q172C-184 | SEQ ID NO: 4 |

-continued

| | | |
|---|---|---|
| SDELRQRCAARLEALKEN | 167-L174C-184 | SEQ ID NO: 5 |
| SDELRQRLCARLEALKEN | 167-R175C-184 | SEQ ID NO: 6 |
| SDELRQRLACRLEALKEN | 167-A176C-184 | SEQ ID NO: 7 |
| SDELRQRLAARLEACKEN | 167-L181C-184 | SEQ ID NO: 8 |
| GEEMRDCARAHVDALRTH | 145-R151C-162 | SEQ ID NO: 9 |
| GEEMRDRARAHVDALRTH | Control wild type 145–162 | SEQ ID NO: 10 |
| GEEMCDRARAHVDALRTH | 145-R149C-162 | SEQ ID NO: 11 |
| GEEMRCRARAHVDALRTH | 145-D150C-162 | SEQ ID NO: 12 |
| GEEMRDRCAHVDALRTH | 145-A152C-162 | SEQ ID NO: 13 |
| GEEMRDRACAHVDALRTH | 145-R153C-162 | SEQ ID NO: 14 |
| GEEMRDRARACVDALRTH | 145-H155C-162 | SEQ ID NO: 15 |
| PVLESFCVSFLSALEEYT | 220-K226C-237 | SEQ ID NO: 16 |
| PVLESFKVSFLSALEEYT | Control wild type 220–237 | SEQ ID NO: 17 |
| PVLCSFKVSFLSALEEYT | 220-E223C-237 | SEQ ID NO: 18 |
| PVLECFKVSFLSALEEYT | 220-S224C-237 | SEQ ID NO: 19 |
| PVLESCKVSFLSALEEYT | 220-F225C-237 | SEQ ID NO: 20 |
| PVLESFKCSFLSALEEYT | 220-V227C-237 | SEQ ID NO: 21 |
| PVLESFKVCFLSALEEYT | 220-S228C-237 | SEQ ID NO: 22 |
| PVLESFKVSCLSALEEYT | 220-F229C-237 | SEQ ID NO: 23 |
| PVLESFKVSFCSALEEYT | 220-L230C-237 | SEQ ID NO: 24 |
| PVLESFKVSFLCALEEYT | 220-S231C-237 | SEQ ID NO: 25 |
| PVLESFKVSFLSCLEEYT | 220-A232C-237 | SEQ ID NO: 26 |
| PVLESFKVSFLSALCEYT | 220-E234C-237 | SEQ ID NO: 27 |
| PVLESFKVSFLSALECYT | 220-E235C-237 | SEQ ID NO: 28 |
| PVLESFKVSFLSALEECT | 220-Y236C-237 | SEQ ID NO: 29 |
| PALEDLRQGLL PVLESFCVSFLSALEEYT KKLN | | SEQ ID NO: 30 |
| PALEDLRQGLL PVLESFKVSFLSALEEYT KKLN | | SEQ ID NO: 31 |
| LKLCDNWDSVTSTFSKLR | 44-L47C-61 | SEQ ID NO: 32 |
| LKLLDNWDSVTSTFSKLR | Control wild type 44–61 | SEQ ID NO: 33 |
| LCLLDNWDSVTSTFSKLR | 44-K45C-61 | SEQ ID NO: 34 |
| LKCLDNWDSVTSTFSKLR | 44-L46C-61 | SEQ ID NO: 35 |
| LKLLCNWDSVTSTFSKLR | 44-D48C-61 | SEQ ID NO: 36 |
| LKLLDCWDSVTSTFSKLR | 44-N49C-61 | SEQ ID NO: 37 |
| LKLLDNWDSVTSTFSCLR | 44-K59C-61 | SEQ ID NO: 38 |
| PALEDLRQGLLP LKLCDNWDSVTSTFSKLR | 209/44-L47C-61 | SEQ ID NO: 39 |
| PALEDLRQGLLP LKLLDNWDSVTSTFSKLR | Control 209/44–61 | SEQ ID NO: 40 |
| PALEDLCQGLLP LKLLDNWDSVTSTFSKLR | 209-R215C-220/44-61 | SEQ ID NO: 41 |
| PALEDLRQGLLP LCLLDNWDSVTSTFSKLR | 209/44-K45C-61 | SEQ ID NO: 42 |
| PALEDLRQGLLP LKCLDNWDSVTSTFSKLR | 209/44-L46C-61 | SEQ ID NO: 43 |
| PALEDLRQGLLP LKLLCNWDSVTSTFSKLR | 209/44-D48C-61 | SEQ ID NO: 44 |

-continued

| Sequence | Description | SEQ ID NO |
|---|---|---|
| PALEDLRQGLLP LKLLDCWDSVTSTFSKLR | 209/44-N49C-61 | SEQ ID NO: 45 |
| PALEDLRQGLLP LKLLDNWDSVTSTFSCLR | 209/44--K59C-61 | SEQ ID NO: 46 |
| GADMEDVCGRLVQYRGEV | 105-R112C-122 | SEQ ID NO: 47 |
| GADMEDVRGRLVQYRGEV | Control wild type 105-122 | SEQ ID NO: 48 |
| GADMEDCRGRLVQYRGEV | 105-V111C-122 | SEQ ID NO: 49 |
| GADMEDVRCLVQYRGEV | 105-G113C-122 | SEQ ID NO: 50 |
| GADMEDVRGCLVQYRGEV | 105-R114C-122 | SEQ ID NO: 51 |
| ARLSRCVQVLSRKLTLKA | 219-G224C-236 | SEQ ID NO: 52 |
| ARLSRGVQVLSRKLTLKA | Control wild type 219-236 | SEQ ID NO: 53 |
| ARLCRGVQVLSRKLTLKA | 219-S222C-236 | SEQ ID NO: 54 |
| ARLSCGVQVLSRKLTLKA | 219-R223C-236 | SEQ ID NO: 55 |
| ARLSRGCVQVLSRKLTLKA | 219-V225C-236 | SEQ ID NO: 56 |
| ARLSRGVQVLSRKCTLKA | 219-L232C-236 | SEQ ID NO: 57 |
| ARLSRCVQVLSRKLTLKAKALHARIQQNLDQLREEL | 219-G224C-254 | SEQ ID NO: 58 |
| ARLSRGVQVLSRKLTLKAKALHARIQQNLDQLREEL | Control 219-254 | SEQ ID NO: 59 |
| ARLCRGVQVLSRKLTLKAKALHARIQQNLDQLREEL | 219-S222C-254 | SEQ ID NO: 60 |
| ARLSCGVQVLSRKLTLKAKALHARIQQNLDQLREEL | 219-R223C-254 | SEQ ID NO: 61 |
| ARLSRGCVQVLSRKLTLKAKALHARIQQNLDQLREEL | 219-V225C-254 | SEQ ID NO: 62 |
| ARLSRGVQVLSRKCTLKAKALHARIQQNLDQLREEL | 219-L232C-254 | SEQ ID NO: 63 |
| ATLKDSLCQDLNNMNKFLEKLR | 51-E58C-72 | SEQ ID NO: 64 |
| ATLKDSLEQDLNNMNKFLEKLR | Control wild type 51-72 | SEQ ID NO: 65 |
| ATLCDSLEQDLNNMNKFLEKLR | 51-K54C-72 | SEQ ID NO: 66 |
| ATLKDCLEQDLNNMNKFLEKLR | 51-S56C-72 | SEQ ID NO: 67 |
| ATLKDSCEQDLNNMNKFLEKLR | 51-L57C-72 | SEQ ID NO: 68 |
| ATLKDSLECDLNNMNKFLEKLR | 51-Q59C-72 | SEQ ID NO: 69 |
| ATLKDSLEQCLNNMNKFLEKLR | 51-D60C-72 | SEQ ID NO: 70 |
| ETGDLWVGCHP | | SEQ ID NO: 71 |
| ETGDLWVGCHPNGMKIFFYDSEN | | SEQ ID NO: 72 |
| LKSLDFNTLVDNISVDP ETGDLWVGCHPNGMKIFFYDSEN | | SEQ ID NO: 73 |
| DWLCAFYDKVAEKLKEAF | 18A-K4C | SEQ ID NO: 74 |
| DWLKAFYDKVAEKLKEAF | 18A control | SEQ ID NO: 75 |
| DCLKAFYDKVAEKLKEAF | 18A-W2C | SEQ ID NO: 76 |
| DWCKAFYDKVAEKLKEAF | 18A-L3C | SEQ ID NO: 77 |
| DWLKCFYDKVAEKLKEAF | 18A-A5C | SEQ ID NO: 78 |
| DWLKACYDKVAEKLKEAF | 18A-F6C | SEQ ID NO: 79 |
| DWLKAFYDKCAEKLKEAF | 18A-V10C | SEQ ID NO: 80 |
| DWLKAFYDKVCEKLKEAF | 18A-A11C | SEQ ID NO: 81 |
| LEKLNSCLRDRLSALTDTPLEELRDSLRSRLDALRST | | SEQ ID NO: 82 |
| LEKLNSCLRDRLSALTDT | | SEQ ID NO: 83 |
| LEELRDSLRSRLDALRST | | SEQ ID NO: 84 |

Preferred peptides are selected from helix 1 (amino acids 44–65), helix 6 (amino acids 145–162) and helix 10 (amino acids 209–238) of apoAI, helix 7 (amino acids 167–184) of apoAI, the helix spanning amino acids 105–122 of apoE3, and amino acids 219–236 of apo AV.

Furthermore, the present invention comprises peptide homologues of the sequences listed above, designed according to the detailed description provided below. The sequences listed above may be modified up to 80% homology without losing the functionality described herein. Furthermore, the sequences of the present invention may be provided with specific cysteine residues engineered into them. These cysteine residues may be substitutes for the residues that are underlined in the sequences listed above. That is, for example, SEQ ID NO: 2, SDEL<u>RQRLAAR</u>LEA<u>L</u>KEN Control wild type 167–184 has, according to the present invention at least one cysteine residue in place of one of the underlined residues.

Furthermore, the present invention comprises methods for making an anti-oxidant peptide based on the design principles outlined in detail in the Detailed Description below. These methods include the steps of identifying an amphipathic helix by known methods for predicting secondary structure and hydrophobicity. See Chou, P. Y., & Fasman, G. D., Adv. Enzymol. Relat. Areas Mci. Bid. 47,45–148, 1978. A Human HDL-associated protein of known amino acid sequence may be used for this purpose. The identification of a helix as amphipathic is carried out using conventional hydrophobicity analyses and helical wheel projections. The alpha helices of the present invention will have between 10 and 100 amino acids, often between 8 and 30 amino acids. Being amphipathic, they will have a hydrophobic side and a hydrophilic side when viewed axially through the helix. As part of the design and synthesis of the present peptides, one may modify at least one residue on the hydrophilic side from the naturally ocurring (wild type) amino acid to a cysteine residue to create a modified helix peptide.

The Human HDL-associated protein may be selected from the group consisting of apoAI, apoE3, apo AV and paroxonase. Alternatively, synthetic or non-natural amino acids may be used in the present peptides.

The anti-oxidant activity is measured by the ability of the modified helix peptide to inhibit lipid peroxidation by soybean lipoxygenase. The ability of the modified helix peptide to inhibit lipid peroxidation by xanthine oxidase and to (not) inhibit xanthine/xanthine oxidase mediated reduction of cytochrome C may also be used to characterize the present peptides. These assays are described in detail in the Detailed Description below.

In general, the present peptides as recited above will provide approximately 50% or more protection against maximum accumulation of lipid peroxides at a concentration of no more than 500 micrograms per mL. They will inhibit oxidation of a lipid or phospholipid alone or with the addition of a water soluble anti-oxidant. The water soluble oxidant may be any known biologically effective antioxidant, such as GSH, vitamin C, vitamin E and N-acetyl cysteine (NAC).

The present peptides may be prepared according to known pharmaceutical technology. They may be administered singly or in combination, and may further be administered in combination with other cardiovascular drugs. They may be conventionally prepared with excipients and stabilizers in sterilized, lyophilized powdered form for injection, or prepared with stabilizers and peptidase inhibitors of oral and gastrointestinal metabolism for oral administration.

BRIEF DESCRIPTION OF THE DRAWINGS

In FIG. 6A, PL micelles were exposed to xanthine/xanthine oxidase (X/Xo, 20 U/ml) in the presence of increasing concentrations of a cysteine-free control peptide (167–184, SEQ ID NO: 2) show no difference in rate of oxidation of lipids as compared to no peptides. FIG. 6B shows results using the thiol-containing apoA-I$_{Milano}$ peptide (167-R173C-184, SEQ ID NO: 1) which show increased antioxidation in a dose-dependent manner. Symbols and doses are the same as in FIG. 5 for Panels A and B. FIG. 6C shows reduction of cytochrome C assay. The synthetic peptides failed to protect cytochrome C indicating that the thiol-containing peptide based on apoA-I$_{Milano}$ is unable to directly quench ROS in the aqueous phase. SOD=superoxide dismutase control.

FIG. 7A: Interaction of peptide 167-R173C-184 with GSH. The combination of GSH plus 167-R173C-184 (triangles) inhibits initial rates of lipoxygenase-mediated lipid peroxidation compared to GSH alone (diamonds) and the apoA-I$_{Milano}$ peptide alone (circles). FIG. 7B: Peptide apoA-I$_{Paris}$ 145-R151C-162 (SEQ ID NO: 9) can stimulate LCAT activation while peptide apoA-I$_{Milano}$ 167-R173C-184 (SEQ ID NO: 1) failed. Results are expressed as a percentage of activation obtained with apoA-I$_{wt}$. FIG. 7C: Peptides unable to stimulate cholesterol efflux from J774 macrophages.

FIG. 8A shows that the thiol containing peptide based on helix 10 of apoA-I inhibits lipoxygenase mediated oxidation of phospholipid in a dose dependent manner similar to the inhibition obtained in FIG. 8B using the 167-R173C-184 peptide. Symbols and doses are the same as in FIG. 5.

In FIG. 9A, PL micelles exposed to xanthine/xanthine oxidase (X/Xo, 20 U/ml), in the presence of increasing concentrations of a cysteine-free peptide related to the apolipoprotein E4 (apoE4) isoform (105–122, SEQ ID NO: 48), show no difference in rate of oxidation of lipids from the absence of peptides. FIG. 9B shows results using the thiol-containing peptide (105-R112C-122, SEQ ID NO: 47) that increasing the peptide concentration inhibits oxidation of phospholipid in a dose-dependent manner where 50% protection is observed at 200 µg/ml. Symbols and doses are the same as in FIG. 5. FIG. 9C shows reduction of cytochrome C (no phospholopids) with X/Xo (squares); triangles X/Xo plus the apoE4 peptide (SEQ ID NO: 48) (400 µg/ml); circles, X/Xo plus the apoE3 peptide (SEQ ID NO: 47) (400 µg/ml). Note the synthetic peptides failed to protect cytochroine C indicating that the thiol-containing peptide (SEQ ID NO: 47) was unable to directly quench ROS in the aqueous phase. The asterisks denote the control SOD (superoxide dismutase).

FIGS. 10A and 10B show the ideal placement of the cysteine residue in an amphipathic alpha helix peptide is at the interface. FIGS. 10C and 10D show alternate positions of the cysteine to be in the hydrophobic or the hydrophilic face.

DETAILED DESCRIPTION OF THE PREFERRED EMBODIMENT

Definitions

Figure 1:
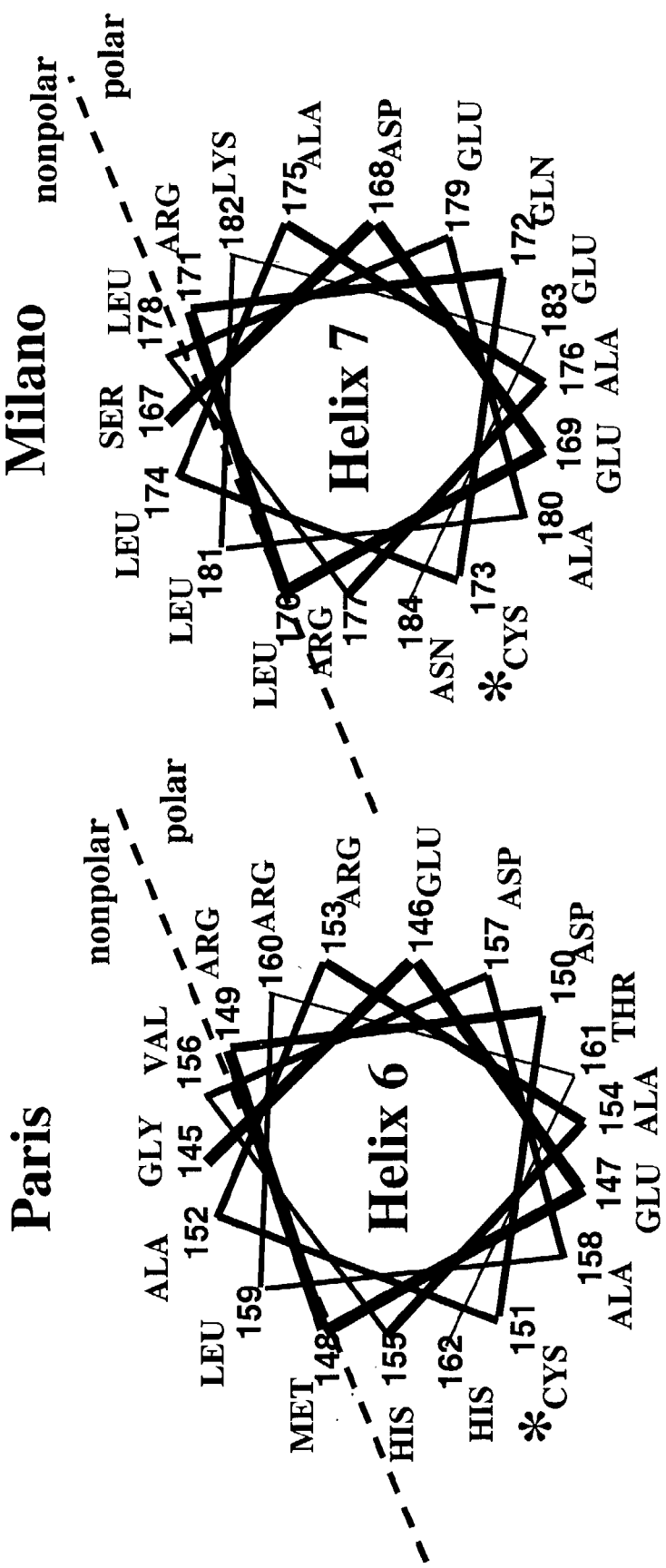
FIG. 1. Helical Wheel Projections of therapeutic peptide mimetics as related to Apolipoprotein A-I$_{pairs}$ (SEQ ID NO:9) and A-I$_{Milano}$ (SEQ ID NO: 1) class A amphipathic alpha helices. Each helix is shown looking through the barrel of the helix. The dotted line represents the hydrophobic/hydrophilic interface which separates the nonpolar from the polar face of the amphipathic helix. The cysteine is labeled with an asterisk to note its proximity to the interface.

The term "peptide" herein is used to describe an amino acid sequence between 2 and 100 amino acids in length, the amino acids being joined by peptide linkages. The amino acids may be naturally and non-naturally occurring.

The term "antioxidant" herein refers to any compound, composition, peptide or protein that inhibits oxidation of phospholipid. A "potent" antioxidant will inhibit oxidation at an effective concentration (EC50) that produces 50% reduction in phospholipid oxidation.

The term "amphipathic" herein refers to a domain which has both a hydrophobic and a hydrophilic surface that are identified, e.g., as described in Kaiser and Kezdy (*Ann. Rev. Biophys. Biophys. Chem.* 16: 561, 1987; Science 223:249, 1984. The term "amphipathic" further means that peptides must exhibit "sidedness" and be amphipathic along the axis through the helix, wherein the majority of the residues on the nonpolar, hydrophobic side of the helix are nonpolar residues, preferably leucine, but may include alanine, valine, isoleucine, proline, phenylalanine, tryptophan and methionine. A majority of the residues on the lipophilic side is preferably made up of hydrophilic residues glycine, serine, threonine, cysteine, tyrosine, asparagines, glutamine, aspartate, glutamate, lysine, arginine and histadine.

The term "homology" or "homologous" means an amino acid similarity measured by the program, BLAST (Altschul et al (1997), "Gapped BLAST and PSI-BLAST: a new generation of protein database search programs", Nucleic Acids Res. 25:3389–3402), as found at http://www.ncbi.nlm.nih.gov/blast/Blast.cgi and expressed as—(% identity n/n). In measuring homology between a peptide and a protein of greater size, homology is measured only in the corresponding region; that is, the protein is regarded as only having the same general length as the peptide, allowing for gaps and insertions.

The terms "derived from" or "based on" mean, regarding a peptide amino acid sequence, having a relationship to a native sequence of an HDL-associated protein.

The term "substantially identical" is herein used to mean having an amino acid sequence which differs only by conservative amino acid substitutions or by non-conservative amino acid substitutions, deletions, or insertions located at positions which do not destroy the biological activity of the peptide.

The term "HDL-associated protein" or "HDL-related protein" means a protein and/or apolipoprotein that is naturally associated with High Density Lipoproteins (HDL), derived from either plasma or interstitial fluids that can be isolated within the HDL density interval (i.e. d=1.063–1.25 g/ml fraction) of co-isolates with apoA-I upon immunoaffinity procedures. Moreover, the said apolipoproteins may also be present in lipid-free form and participate in HDL metabolic pathways including the ABCA1 cholesterol efflux pathway which gives rise to HDL particles.

The term "Class A amphipathic alpha helix" refers to an alpha helix in which one surface of the peptides is composed primarily of hydrophobic amino acids and the other surface hydrophilic amino acids. Class A alpha helices possess positively charged amino acids on the polar surface next to the interface of the hydrophobic domain, and negatively charged residues in the middle of the polar surface.

The term "Class Y alpha helices" refers to an alpha helices which are amphipathic, exhibiting a broad nonpolar surface and a hydrophilic domain that lacks interfacial positively charged residues.

Introduction

Cardiovascular disease is the number one cause of death in western societies and the prevalence of this disease is increasing worldwide. One of the strongest predictors of risk is the plasma concentration of high-density lipoprotein (HDL) which exhibits an inverse relationship. Despite the strong epidemiological data relating increased plasma HDL to protection from cardiovascular disease, a number of rare mutations in apolipoproteinA-I, the major protein of HDL, present an HDL deficiency and resistance to cardiovascular disease. Apolipoprotein A-I$_{Milano}$ (apoA-I$_{Milano}$) and Apolipoprotein A-I$_{Paris}$ (apoA-I$_{Paris}$) are rare, naturally occurring Arg→Cys substitutions in apoA-I primary sequence that manifest such a HDL deficiency, but affected subjects do not develop cardiovascular disease. The cysteine mutations enable apolipoprotein dimerization via a disulfide bridge. This dimerization limits HDL particle growth and facilitates the clearance of HDL from the circulation. Indeed, human carriers of apoA-I$_{Milano}$ exhibit a HDL deficiency and mild triglyceridemia. The paradox of HDL deficiency and protection from cardiovascular disease has led to the suggestion that the cysteine substitution for arginine in the lipid-binding domain of apoAl may impart redeeming qualities protecting the artery wall from athermatous lesion formation.

The inventor reported, for the first time, in *Biochemistry* 41, 2089–2096 (2002), a unique antiatherogenic function of apoA-I$_{Milano}$ and apoA-I$_{Paris}$ related to antioxidant properties on phospholipid surfaces. The results of the studies indicate that apoA-I$_{Milano}$ and apoA-I$_{Paris}$, were potent inhibitors of lipid peroxidation protecting phospholipid surfaces from lipophilic, as well as, water soluble free radical initiators; whereas, apoA-I$_{WT}$ was a relatively poor inhibitor of oxidative events.

Using purified recombinant apolipoproteins and enzymatic methods of phospholipid peroxidation it was demonstrated that apoA-I$_{Milano}$ (R173C) and apoA-I$_{Paris}$ (R151C) exhibited antioxidant activities not associated with wild-type apoA-I. This antioxidant activity was attributed to the monomeric form of apoAI$_{Milano}$ and apoA-I$_{pans}$ and was found to be dependent on the presence of phospholipid. The latter is based on studies where apoA-I$_{Milano}$ and a synthetic peptide mimetic were unable to prevent superoxide anion induced reduction in Cylochrome C (FIG. 6C).

This observation has important implications regarding the underlying mechanism by which cysteine containing amphipathic alpha helices in the exchangeable apolipoproteins exert antioxidant activity and protect against inflammatory related disease. Xanthine/xanthine oxidase generates superoxide anion and hydroxyl radicals in the aqueous phase that mediate the oxidation of phospholipid. The fact that apoA-I$_{Milano}$ was unable to prevent xanthine/xanthine oxidase mediated reduction of cytochrome C suggests that in lipid-free form apoA-I$_{Milano}$ was unable to quench reactive oxygen species in lipid-free form. This indicates that apoA-I$_{Milano}$ (and its synthetic peptide mimetics) act on the phospholipid to inhibit the initiation/amplification of lipid peroxidation via a mechanism probably related to chain-breaking antioxidant activity. By extension of these observations, one can infer that antioxidant activity is directed toward lipid surfaces which links the antioxidant activity of apoA-I$_{Milano}$ to the ABCA1 transporter that is required for the lipidation of apolipoproteins in vivo. This provides a basis for drug development in which synthetic peptides can be engineered to possess both the lipidation properties of the native apolipoproteins and the novel antioxidant activity discovered for apoA-I$_{Milano}$. As a result, it is feasible to specifically target the therapeutics to sites of inflammation and cholesterol deposition where there is an upregulation in the ABCA1 transporter to specifically deliver potent antioxidant activity to sites where its needed most to prevent inflammatory related disease initiation.

The gene for human Apolipoprotein A-I (Apo A-I) had been previously cloned. The entire sequence for the human Apo A-I protein is found at SEQ ID NO:85. Certain mutations in this gene have been identified at the molecular level, such as Apolipoprotein A-I$_{Milano}$ (Apo A-I$_{Milano}$) (R173C) and Apolipoprotein A-I$_{paris}$ (Apo A-I$_{paris}$) (R151C).

Using the observation that a free thiol positioned at the hydrophobic/hydrophilic interface of an amphipathic alpha helix confers chain breaking antioxidant activity associated with an inhibition in lipid peroxide amplification on phospholipid surfaces, permits the design and synthesis of peptides that have anti-oxidant activity and which thereby allow prevention of inflammatory events associated with the onset of CVD and other diseases.

Designing peptides that exhibit antioxidant activity that are active only upon lipidation in effect enables these peptides to be targeted to areas where there is inflammation and cholesterol deposits. The synthetic peptides based on apoA-I$_{Milano}$ and apoA-I$_{Paris}$ bind to lipid surfaces and exert the antioxidant characteristics of the full-length variants. These specific peptides do not promote cholesterol and phospholipid efflux from cells indicating that they are useful as anti-inflammatory agents directed towards preformed HDL and metabolic pathways linked to HDL metabolism. Utilizing information based on the position of the cysteine residue at the polar/nonpolar interface of amphipathic alpha helices, it is possible to create peptides derived from different amphipathic alpha helices of apoA-I which are known to exert cholesterol efflux properties. These specific sequences include, but are not limited to helix 1 (aa 44–65) and helix 10 (aa 209–238) which do mediate the lipidation process establishing a specific link to the ABCA1 transporter. This acts as an entrance to the pathway whereby the ABCA1 receptor, which is responsible for HDL assembly in the artery wall, is upregulated upon cholesterol enrichment of cells. As a result, it is possible to couple the lipidation properties of native apoA-I with the phospholipid directed antixodant activity of apoA-I$_{Milano}$ in the form of a synthetic peptide that specifically targets metabolically active sites of cholesterol deposition thus inhibiting inflammatory events involved in early disease progression.

Structural analyses revealed identical placement of a cysteine residue at the polar/nonpolar interface of an amphipathic alpha helix within apoE3 thus defining the mechanism for the antioxidant activity of apoE3. A similar "motif" in apoAV is also used to create new peptides. Thus the current peptides take advantage of a unifying structural domain that confers a newly discovered beneficial activity to a broad spectrum of apolipoproteins that exhibit diverse anti-inflammatory activities. This novel feature of specific cysteine placement within amphipathic alpha helices thus provides the basis for the development of therapeutic agents that have wide applicability to prevent the onset of a number of inflammatory related diseases including atherosclerosis, Alzheimer's disease, and osteoporosis.

Moreover, these peptides have been designed to have both native properties of HDL-associated proteins and the newly discovered antioxidant property. Because the present peptides are based on naturally occurring proteins, they are expected to have above average safety and efficacy profiles.

Additional peptides are derived from different amphipathic alpha helical repeats of apoA-I including Class Y helices, and combinations thereof, to create novel peptides that possess the native properties of apoA-I in promoting cellular cholesterol efflux in addition to the novel antioxidant activity of apoA-I$_{Milano}$. This will effectively target peptides to sites of cholesterol deposition and inflammation where there is an upregulation in ABCA1 cholesterol transporter expression. (The ABCA1 transporter is a recently discovered HDL receptor located on aortic macrophages associated with Tangier's Disease and is responsible for the synthesis of HDL in the artery wall.) This is made possible by the unique antioxidant property of the synthetic peptides which is conferred upon lipidation on phospholipid surfaces as well as the ability to incorporate a free cysteine residue within different classes of amphipathic alpha helices. As a result the peptides can be used in combinations with other therapeutic regiments that promote an unregulation in ABCA1 to effectively target to therapeutic peptides to sites of inflammation and cholesterol deposition.

A. Basic Peptide Mimetic Features

Figure 2:
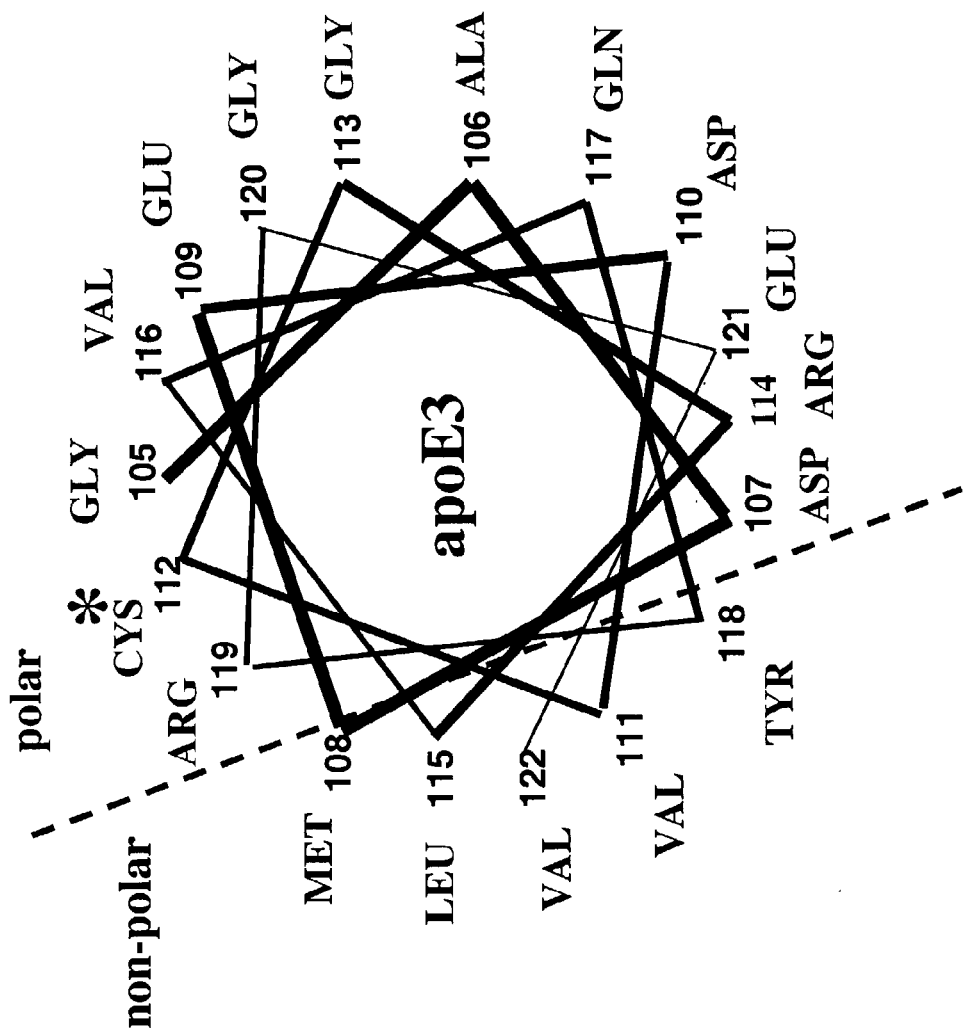
FIG. 2. Helical Wheel Projection of therapeutic peptide mimetic related to Apolipoprotein E3 (SEQ ID NO:47). The helix is shown looking through the barrel of the helix. The dotted line represents the hydrophobic/hydrophilic interface which separates the nonpolar from the polar face of the amphipathic helix. Cysteine1 112 is labeled with an asterisk to note its proximity to the interface.
Figure 3:
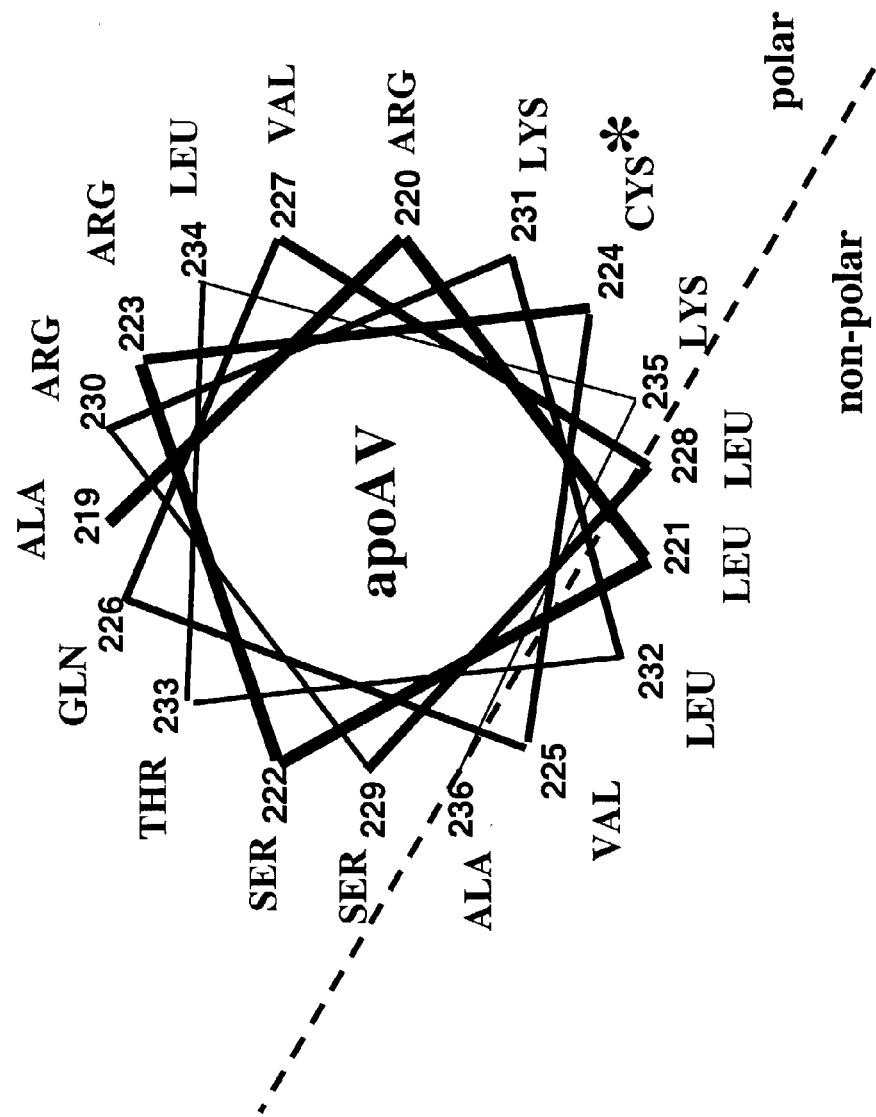
FIG. 3. Helical Wheel Projection of synthetic peptide related to the antioxidant domain of Apolipoprotein A-V (SEQ ID NO:52). The helix is shown looking through the barrel of the helix. The dotted line represents the hydrophobic/hydrophilic interface which separates the nonpolar from the polar face of the amphipathic helix. Cysteine224 is labeled with an asterisk to note its proximity to the interface.

The helical wheel projections in FIG. 1 indicate the position of R173C and R151 within amphipathic alpha helices 6 (residues 145–162) and 7 (residues 167–184) of apoA-I. FIGS. 2 and 3 indicate similar positioning of R112C and C224 in amphipathic alpha helices of apoE3 and apoAV, respectively. Each helix is shown looking down the barrel of the helix. The hydrophobic/hydrophilic interface is drawn as the dotted line to separate the polar from the nonpolar face of the amphipathic helix. The nonpolar face is the helix is the side and site of lipid interaction, while the polar face interacts with water and water-soluble free radical initiators.

The cysteine substitutions for arginine in FIG. 1 correspond to apoA-I$_{Milano}$ (helix 7) and apoA-I$_{Paris}$ (helix 6). The substitutions are located near the interface of the hydrophobic/hydrophilic surfaces of their respective amphipathic alpha helices. This unique location of the cysteine residue near the hydrophobic/hydrophilic interface demonstrate that cysteine substitutions at strategic loci on the amphipathic alpha helices of HDL-associated proteins can protect phospholipids from water soluble free radical initiators in addition to lipoxygenase-mediated mechanisms which occur on phospholipid surfaces. Moreover, the apparent water accessibility of the free thiol allows for important interactions with water-soluble antioxidants enhancing the antioxidant activity of apoA-I$_{Milano}$ and its peptide mimetics.

Based on this model, the peptides of this invention take advantage of this observation and direct the design of peptides that have a cysteine residue present at the polar/nonpolar interface of an amphipathic alpha helix. The generated peptide should thereby exhibit an antioxidant property which can thus protect phospholipids from water soluble free radical initiators.

Since a goal of this invention is to form peptide mimetics that are derived from naturally occurring proteins, so as to be safe and not prone to eliciting an immune response in a patient, it is preferred that the present peptides are derived from HDL-associated proteins. Appropriate HDL-associated proteins include but are not limited to, Apolipoprotein A-I, Apolipoprotein A-V, Apoliproprotein E3, Apolipoprotein E4, Human Serum Paraoxonase and their variants. As each of these proteins is associated with HDL and exhibit the same apparent structural motif, the current peptides of this invention are derived from specific amphipathic alpha helices in these proteins that known to possess cysteine residues and/or derived from helical segments engineered to possess a free cysteine at the polar/nonpolar interface of amphipathic alpha helices.

Figure 4:
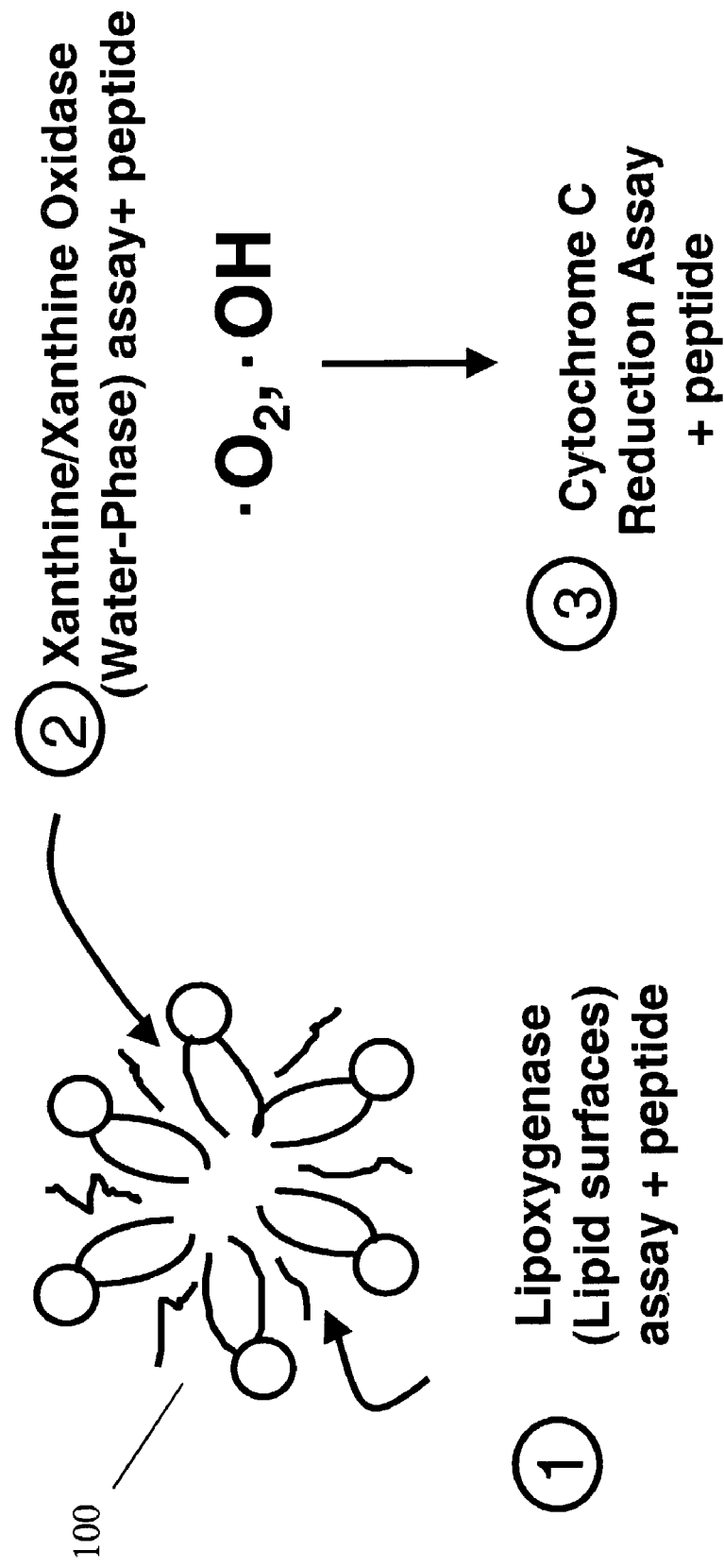
FIG. 4. Schematic showing protocol for determining the antioxidant activity of synthetic peptide mimetics which sets criteria for peptides useful in the invention. The peptides are first added to a lipoxygenase assay to observe the rate of lipid peroxidation of micelles (100). The micelle substrate (100) is composed of 1-palmitoyl-linoleoylphosphatidylcholine and dispersed in deoxycholate and Borate (pH=9.0)/saline-EDTA. Second, the peptides are added to an assay having xanthine/xanthine oxidase to observe the rate of lipid peroxidation of micelles (100). Thirdly, the peptides are added to an assay to determine whether the peptides directly quench reactive oxygen species and prevent cytochrome reduction.

It is also important that the peptides that are created meet with the following criteria, that they 1) exhibit antioxidant activity that is directed toward lipid surfaces, 2) be unable to quench water-soluble free radicals in the absence of lipids and 3) have potential interactions with water-soluble antioxidants. These peptides can be tested to meet this criteria through several simple experiments which take minutes to complete. FIG. 4 outlines these three simple assays used to define that antioxidant characteristics of each peptide. The assay to test antioxidant activity directed toward lipid surfaces can be test using the assay described in Example 3. The assay in Example 4 can be used to test potential interactions with other water-soluble antioxidants and the Cytochome C reduction assay. Example 7 can be used to test whether the peptide is unable to quench water-soluble free radicals absent lipids. Other assays that are disclosed in Examples 4 and 5, which test whether the peptide is capable of LCAT activation or cholesterol efflux from cells, are used to determine whether the peptides exhibit the native properties of the protein from which the peptides is based on.

Figure 5:
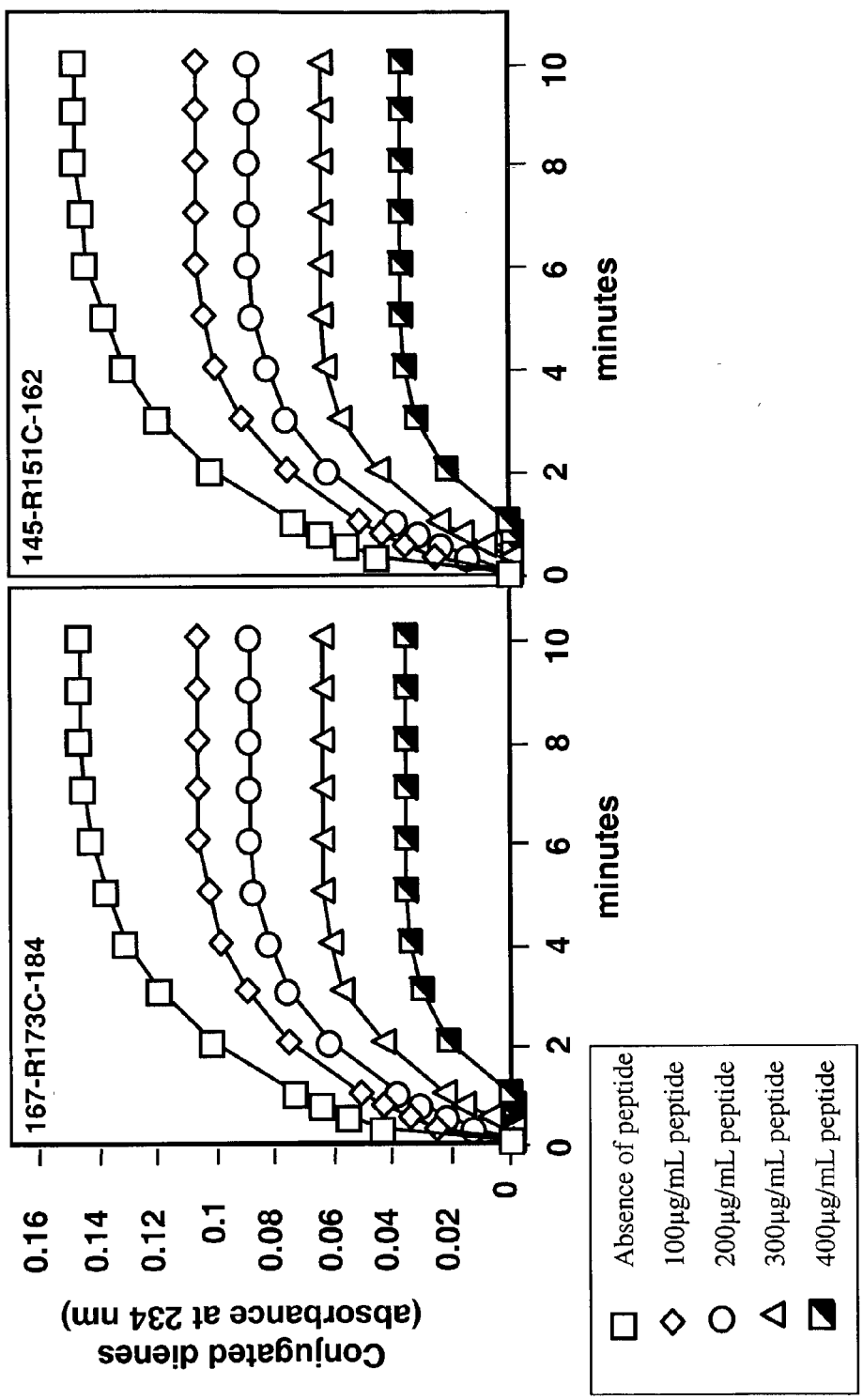
FIG. 5. Graphs showing antioxidant activity of peptide mimetics of the apoA-I$_{Milano}$ peptide (SEQ ID NO: 1 in FIG. 5A) and the apoA-I$_{Paris}$ peptide (SEQ ID NO: 9 in FIG. 5B). Phospholipid (PL) micelles were exposed to reactive oxygen species (ROS) generated via xanthine/xanthine oxidase (X/Xo, 20 U/ml) in the absence (squares) or presence of increasing concentration of the synthetic 18-mers: diamonds, circles, triangles and hatched squares denote 100, 200, 300, and 400 μg/mL concentrations. Results show that the peptides exhibit antioxidant activity in dose-dependent manner. Results show that the peptides exhibit antioxidant activity in dose-dependent manner where approximately 50% protection against lipid peroxidation is observed using 200 μg/ml.

Preferably these peptides should exhibit a percent protection of phospholipids from oxidation at a concentration that is at least the same level of the apoA-I Milano and Paris variants as shown in FIG. 5. Therefore, suitable peptides should exhibit at least a 50% protection against maximum accumulation of lipid peroxides at a concentration of preferably no more than 200 µg/mL. The peptides should more preferably exhibit 50% protection of maximum accumulation of phospholipids at a 250 µg /mL concentration, even more preferably no more than 300 µg/mL, and even more preferably no more than 400 µg/mL of peptide, and most preferably at concentrations no greater than 500 µg/mL.

The peptides may be made and purified by methods known in the art, preferably by in vitro automated synthesis, but also by recombinant DNA methods. Furthermore, these peptides can be synthesized using L-amino acids, non-natural or other modified amino acids, as is known in the art, in order to synthesize peptides which can act upon targets in the body and be degraded, yet do not interfere with normal protein function. The peptides can be stored in lyopholized form and dissolved in aqueous buffers or water prior to use. For the purposes of experimental use, the peptides are dissolved in sterilized degassed buffers to optimize biological activity which remains stable over 1–3 months at 4° C.

The synthetic peptides of the present invention could contain at least 1–4 cysteine residues. In place of cysteine, other residues may be employed that also contain a reducing moiety, namely a thiol (SH) group. Creating peptides with other thiol-bearing moieties would confer an increased nucleophilicity and thereby increase the ability to reduce free radicals. However, this could potentially interfere with important interactions with water-soluble antioxidants and thus limit potential use in humans.

B. Designing Peptides from HDL-Associated Proteins

The starting point for the present model is Apolipoprotein A-I and other HDL-associated proteins. As shown in the sub-sequences in Examples 7–13, the present peptides are derived from several regions of the wild-type Apo A-I protein (SEO ID NO:85), Apolipoprotein E3 (SEO ID NO:86), Apolipoprotein A-V (SEO ID NO:87) (*Science* 294:169–173) and Human Serum Paraoxonase (PON) (SEO ID NO:88), particularly regions that have amphipathic alpha helices that contain a cysteine residue at the polar/nonpolar interface.

Good candidates for peptides useful in the invention are peptides based on protein domains of HDL-associated protein molecules that are amphipathic alpha helices having a cysteine at the hydrophobic/hydrophilic interface because such regions are most likely to interact with lipid surfaces and be able to confer antioxidant activity. Generally, the helical segments are marked at their boundary by proline residues. Helical wheel projections as shown in FIG. 1–3 are constructed to define the position of the cysteine residue at the polar/nonpolar interface of the helix. Additional helical segments not known to possess cysteine residues are used because their unique qualities that permit lipidation (i.e. allow the peptides to promote cholesterol efflux from cells such as J774 macrophages). Important helical segments are identified based on published information (*J. Bid. Che,.* 274: 2021–2028) include helix 1 (aa 44–65) and helix 10 (aa 209–238) of apoA-I that are important in the nucleation of lipidation.

C. Cysteine Placement that Influences Antioxidant Activity

Peptides based on helix 1 and helix 10 of apoA-I can be used in the form of a single 18-mer in which a cysteine residue has been strategically added to the polar/nonpolar interface of the amphipathic alpha helix as in apoA-$I_{Milano}$. The position of the cysteine residue is set between 1 and 4 amino acids off the interface to mimic the position in the natural variants. In an idealized model peptide (18-mer) in which the numbering represents a consecutive sequence of amino acids 1–18, the cysteine can be placed at positions 7, 11, 18 or 5, 9, or 16 depending on the positioning of the nonpolar face of the helix in the native structures defined by the helices derived from apolipoproteins with known cysteine residues such as apoA-$I_{Milano}$ and apoA-$I_{Paris}$. However, this generalized numbering scheme may not apply to all helices such as helix 1 of apoA-I (aa 44–61) where the cysteine can be placed at positions 4, 11, 18 or 2, 6, 13 to mimic the natural positioning of the cysteine residue at the interface of amphipathic alpha helices. But, in generalized terms, the cysteine residue can be placed between 1–4 residues off the interface of the helix to confer thiol dependent antioxidant activity.

Figure 6:
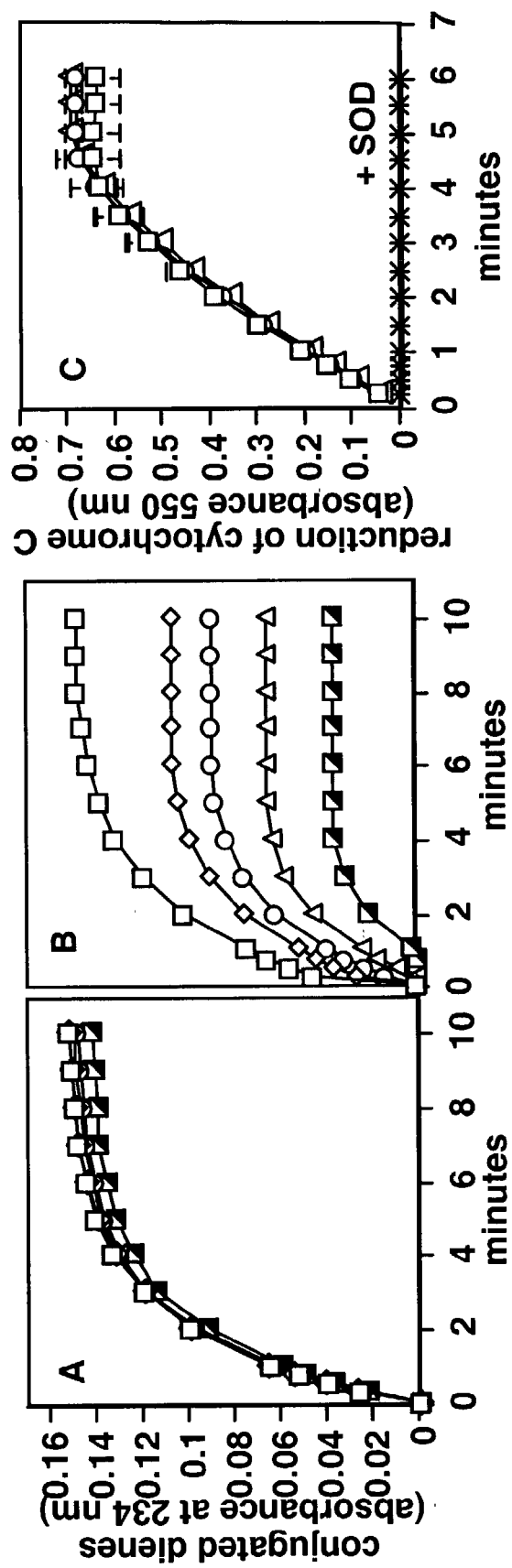
FIG. 6. Graphs showing antioxidant activity of apoA-I$_{Milano}$ peptide 167-R173C-184 inhibits oxidation induced via ROS.
Figure 8:
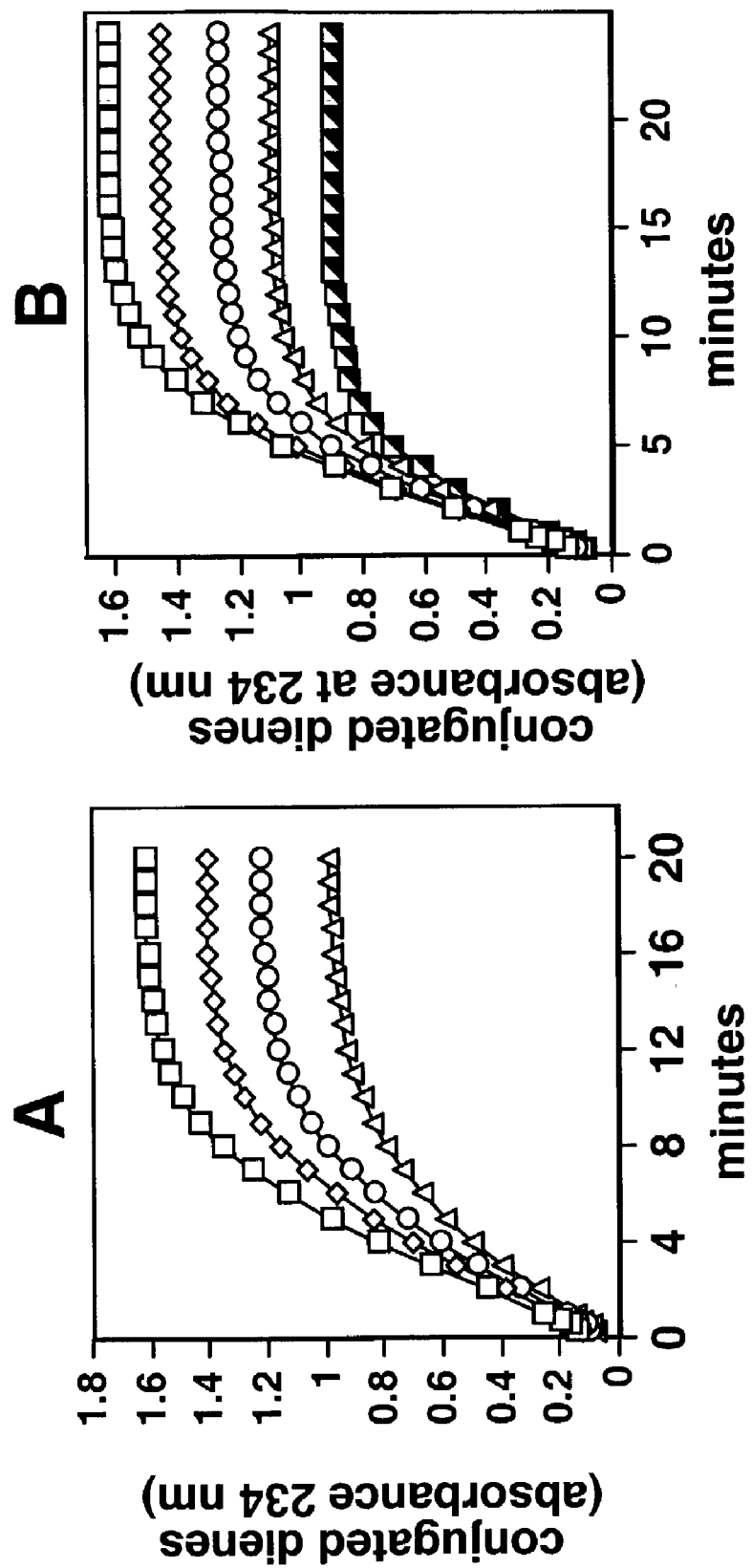
FIG. 8. Graphs show antioxidant activity of a cysteine containing peptide related to Helix 10 of apoA-I (220-K226C-237, SEQ ID NO: 16).
Figure 9:
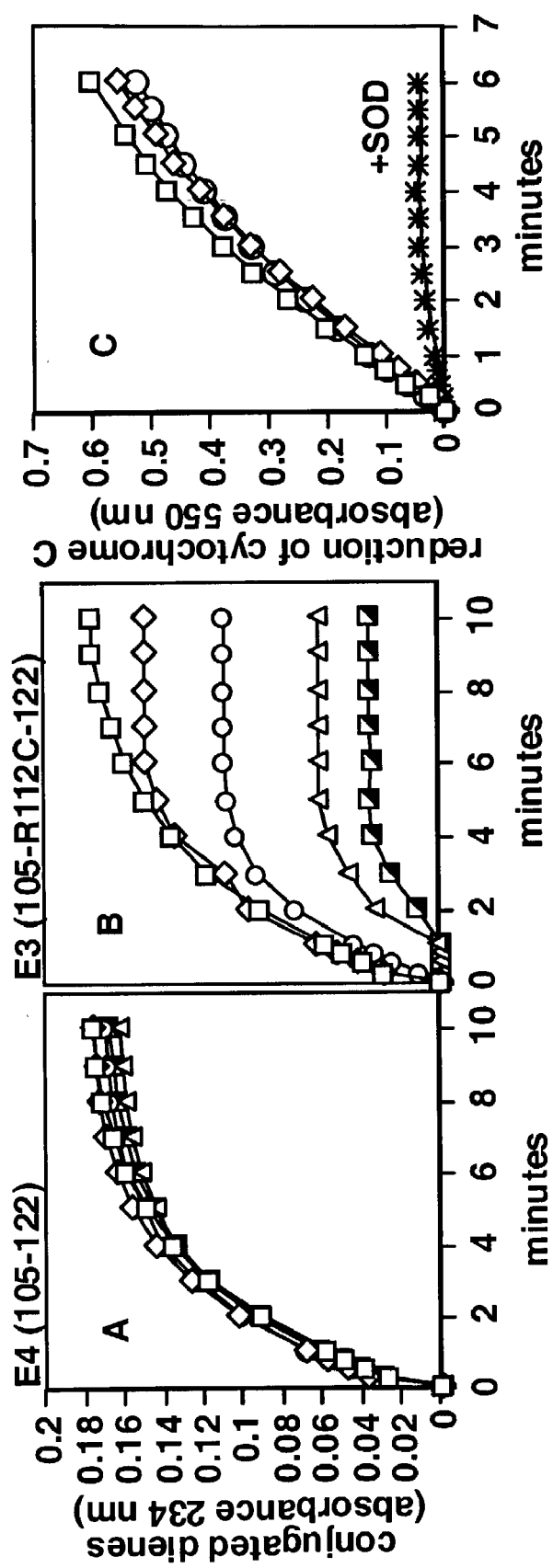
FIG. 9. Graphs showing antioxidant activity of a synthetic peptide based on helix 3 of apolipoprotein E-3 (105-R112C-122, SEQ ID NO: 47).

The ability to utilize amphipathic alpha helices that are not known to possess a cysteine residue, such as helix 1 and 10 of apoA-I, is based on the following observations: 1) the synthetic peptides derived from helix 6 and 7 of apoA-$I_{Milano}$ and apoA-$I_{Paris}$ (peptides SEQ ID NO: 1 and SEQ ID NO: 9, respectively) as well as the peptide derived from apoE3 all possess the same antioxidant characteristics despite the fact that they differ in primary amino acid sequence (data shown in FIGS. 5, 6 and 9). This highlights the critical contribution of specific cysteine placement which is conversed in each of the parent apolipoproteins. 2) A cysteine residue added to the polar/nonpolar interface of helix 10 of apoA-I (peptide SEQ ID NO: 16) possesses antioxidant activity similar to the peptide derived from apoA-$I_{Milano}$ (data shown in Example 8 and FIG. 8).

Specific placements of a free cysteine residue render the amphipathic peptide relatively protected against free radical mediated oxidation of phospholipid. The free thiol group does not directly quench the free radical, but instead prevents the initiation/amphification of lipid peroxidation.

There are three categories that represent specific placement of cysteine residues around the face of an amphipathic alpha helix as shown in the helical wheel projection of an 18-mer peptide in FIGS. 1–3. First, placement of a cysteine residue at the polar/nonpolar interface of the helix (i.e. 1–3 amino acids away from the interface as judged by the two dimensional face of the wheel projection) renders the peptide fully effective as an antioxidant when oxidation is initiated in the water phase or on the phospholipid surface. Utilizing a generalized number scheme for the sequence of amino acids (1–18) in an 18 mer peptide, peptides can be engineered from the following apolipoproteins where the position of the cysteine residues in noted by numeric position: apoA-$I_{Milano}$ and apoA-$I_{Paris}$ based peptides, positions 7, 11, 18 or 5, 9, 16; ApoE3 based peptides, positions 4, 8, 15 or 3, 7, 10; apoAV based peptides, positions 4, 11, 15 or 6, 13, 17; generic peptide I (18-A) based peptides, 4, 8, 15 or 2, 9, 13; and the generic sequence II, positions 7, 11, 18 or 5, 9, 16.

Second, placing the cysteine residue in middle of the hydrophobic or hydrophilic face of the helix may impart functionality or result in loss of functionality.

Third, peptides with multiple cysteines may be made by placing cysteines at the hydrophobic/hydrophilic interface, as well as in either the hydrophobic or hydrophilic faces of the helix. Such changes in placement of the cysteine residue is predicted to specifically alter the functionality of the peptides in a systematic fashion. This can lead to the creation of a generic amphipathic alpha helix for the development of tailor-made pharmacteuticals of defined functionality including specific antioxidant activity attributed to strategic cysteine placement, LCAT activation properties endowed via arginine clustering at the polar/nonpolar interface, and cholesterol efflux properties obtained by either phenylalanine placement or by combining unique helical segments.

Figure 10:
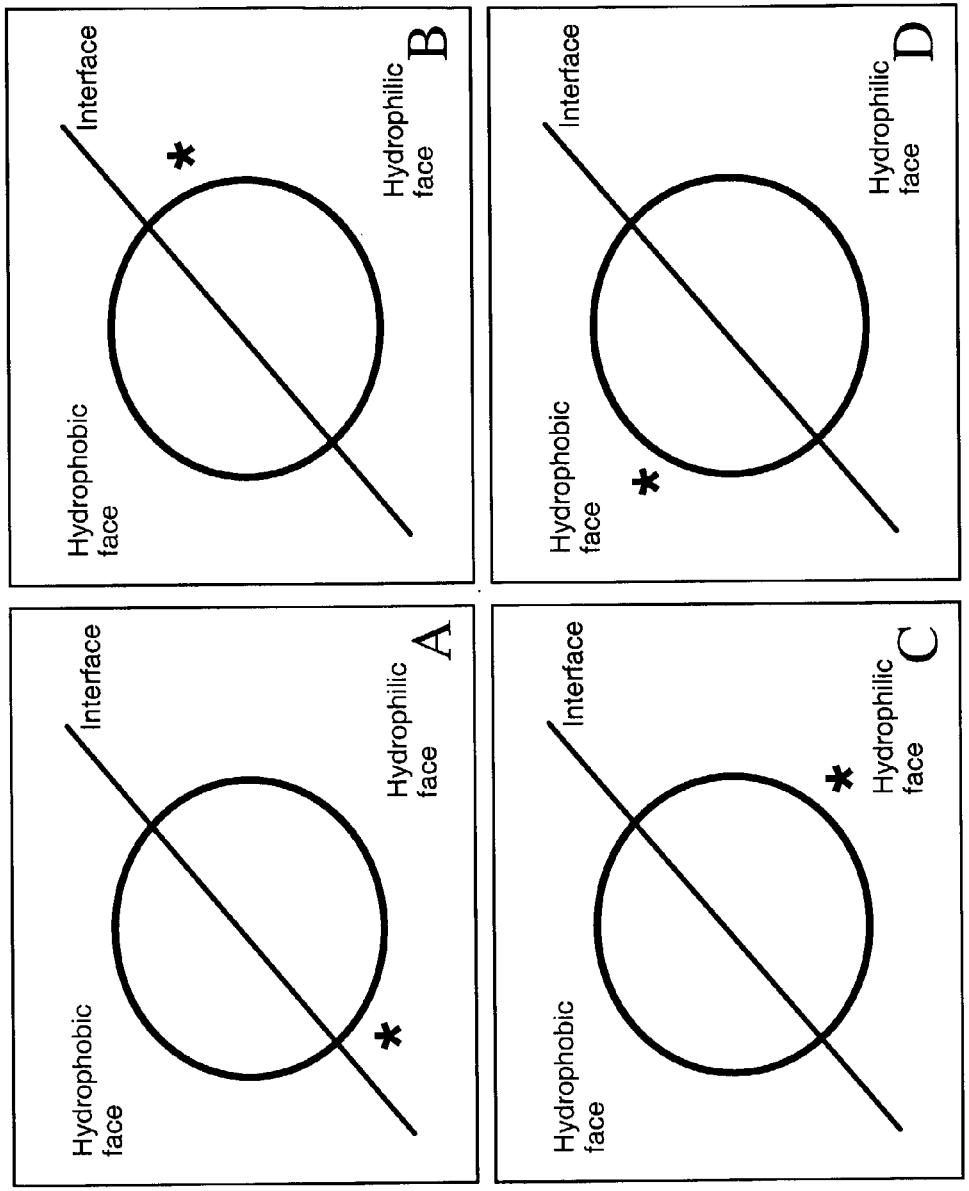
FIG. 10. Representation of the general placement of a thiol-bearing residue in peptide mimetics.
Figure 11:
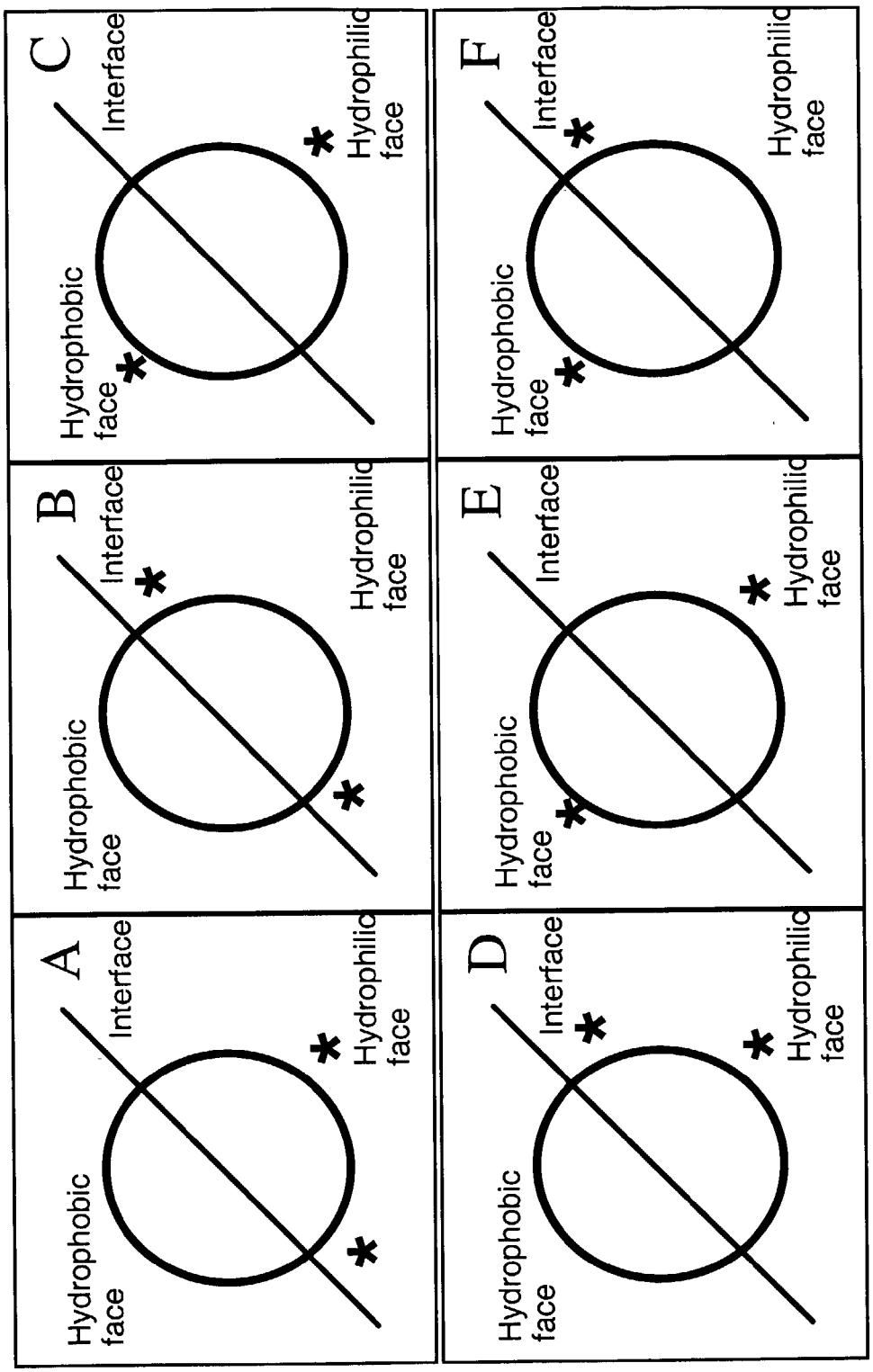
FIG. 11. Representation of the general placement of multiple thiol-bearing residues in synthetic peptides. Cysteine residues can be placed on the same side of the interface as in FIGS. 11A, 11B, and 11D, or on opposite sides of the amphipathic interface as in FIGS. 11C, 11E and 11F.

The generalized placement of a cysteine at the polar/nonpolar interface of amphipathic alpha helix is represented in FIGS. 10 and 11. FIGS. 1–3 also illustrate the conservation of the cysteine placement in apoA-$I_{Milano}$, apoA-$I_{Paris}$, apoE3 and apoAV. In some instances the specific cysteine placement disrupts salt bridges which may be important for allowing increased mobility of the free thiol at the hydrophobic/hydrophilic interface. This is true for peptides based on apoA-$I_{Milano}$, apoA-$I_{Paris}$ and apoE3 which result from R→C interchanges in class A amphipathic alpha helices.

By definition, class A amphipathic alpha helices possess positively charged amino acids such as arginine (R) at the interface of the polar/nonpolar surface of the helix which may be important in designing therapeutic peptides. In general, the positioning of the cysteine is positioned near the interface either 1–3 or 1–4 amino acids off the interface into the aqueous phase which may be utilized to generate a peptide with antioxidant activity. Antioxidant activity of peptides, wherein the cysteine is placed further away from the nonpolar surface, may be influenced by the overall lipid binding affinity of the helical segment and its ability to penetrate into phospholipid surfaces. Lipid binding affinity is influenced by the contribution of specific hydrophobic amino acids located in the nonpolar face of the helix as well as the distribution of positively charged residues such as lysine and arginine residue in the polar surface promote electrostatic interactions with phospholipids.

An important feature of some of the synthetic peptides is the movement of the cysteine to the middle of the nonpolar surface of the helix which, in and of itself, may not influence antioxidant activity of the individual synthetic peptide. But such peptides are theorized to lack specific interactions with water-soluble antioxidants that enhance antioxidant activity of the thiol-containing apolipoproteins, such as apoA-$I_{Milano}$, and their peptide mimetics. Loss of such important interactions would generate an important series of peptide mimetics that could be used experimentally to determine whether such interactions are important in preventing inflammatory related diseases, thereby allowing the identification of new drug targets and permitting future drug design.

In general, the free cysteine residue can be moved around the face of the helix in single-turn fashion as illustrated in the peptide based on apoA-$I_{Milano}$. The natural position of the cysteine residue in apoA-$I_{Milano}$ (helix 7, aa 167–184) is found at position 173. Movement of the thiol around the face of the helix is achieved via specific placement at 171 (located at the opposite interface), 172 (thiol positioned in the middle of the hydrophilic surface), and 174 (thiol positioned in the middle of the hydrophobic surface). However, it is possible that cysteine placement at other interfacial sites confers antioxidant activity and it is possible that other sites towards the middle of the hydrophobic surface are useful in designing peptides.

Moreover, various placement schemes are used to create peptides containing two or more free cysteine residues. For example, peptides can be engineered to possess two or three thiols: one in the water face of the helix, one in the lipid face, and one at the polar/nonpolar interface. General examples of the structural placement of multiple cysteine residues are represented in FIG. 11. This last strategy of cysteine placement is to be used with caution as the multiple cysteines may serve to dilute the specificity and unique properties of the peptides rather than enhance their antioxidant properties.

D. Extending the Peptides

The present peptides are based on a modeled amphipathic alpha helical structure. Accordingly, they may be from about 12 to 100 amino acids in length, preferably 18–40 amino acids in length, more preferably 18–20 amino acids in length. The peptide subsequences can be extended in either the amino and carboxy direction or both, with the sequence from the native protein from which the peptide was derived.

When extending the peptides, in one embodiment, beyond the peptide amphipathic helix in the amino and/or carboxy directions, it is preferred that the sequence of the native Apo A-I, as set forth in SEQ ID NO:85, is used. In a separate preferred embodiment, the sequences of native Apolipoprotein E3 (apoE3) as set forth in SEQ ID NO:86, Apolipoprotein A-V (apoAV) as set forth in SEQ ID NO:87, or human serum paraoxonase (PON) as set forth in SEQ ID NO:88 are used to extend the peptide.

The extended sequence need not be identical to the recited sequences above, however it should be substantially identical, preferably at least 80% homologous.

In another preferred embodiment, multiple amphipathic alpha helical peptides having cysteine substitutions can be used to extend the peptides to create a larger peptide in which multiple domains have antioxidant properties. See Example 8, specifically SEQ ID NOS: 30,31, 39–46.

Depending upon what the targeted disease, proteins and events are will dictate which sequence is used to extend the peptides. For example, if the targeted oxidation events are related to Alzheimer's Disease, then the peptide should probably be extended with sequence having homology to apoE3. If the targeted oxidation events are related to atherosclerosis, the peptide can be extended with the sequences homologous to apoA-I or PON.

E. Applications and Therapeutics

These peptides make feasible the preparation and administration (either orally or intravenously) of agents that carry the beneficial properties of the full length apoA-I$_{Milano}$ and apoA-I$_{Paris}$ proteins. The present peptides may be used to prevent CVD in the general population, based on this newly described activity associated with the presence of the free thiol in the monomeric form of apoA-I$_{Milano}$ and its peptide mimetics. Therapeutics derived from the dimeric form of the variant, which lacks the antioxidant activity attributed to the monomeric form of the variant, is currently in pharmaceutical development. The present antioxidant peptides are also useful in preventing ischemia following bypass surgery and/or after myocardial infarction, since the present peptides move into and out of artieries with lipoproteins such as HDL. A recently discovered HDL receptor located on aortic macrophages is associated with Tangier's Disease (the ABCA1 transporter) and is responsible for the synthesis of HDL in the artery wall. In one embodiment, the present peptides may be used to promote cellular cholesterol removal from macrophages in the arterial wall via ABCA1.

The present peptides may be prepared according to known pharmaceutical technology. They may be administered singly or in combination, and may further be administered in combination with other cardiovascular drugs. They may be conventionally prepared with excipients and stabilizers in sterilized, lyophilized,powdered form for injection, or prepared with stabilizers and peptidase inhibitors of oral-and gastrointestinal metabolism for oral administration.

EXAMPLE 1

Preparation of Synthetic Peptide Mimetics

Synthetic peptides were engineered from the monomeric forms of apoA-I$_{Milano}$, apoA-I$_{Paris}$ and apoE3. Peptides which lacked cysteine residues were developed from wild-type apoA-I and the apoE4 isoform and served as controls. All peptides were purchased from Biosynthesis Incorporated (Lewisville, Tex.) and were modified by an N-terminal acetyl group and C-terminal amide group. Peptides were dissolved in sterile, filtered, degassed 10 mM Tris-buffered (pH=8.0) Saline EDTA (2.7 mM) and stored at 4° C. The antioxidant activity of the thiol-containing peptides remained stable over a 3 month period when stored in this manner.

EXAMPLE 2

Micelle Substrate to Test the Antioxidant Activity of the Peptides

A schematic showing the assays used for determining the antioxidant activity of synthetic peptide mimetics is shown briefly at FIG. 4. Assays 1 and 2 utilize a micelle substrate composed of 1 mM 1-palmitoyl-2-linoleoylphosphatidyl-choline dispersed in Borate (0.2 M) buffered (pH=9.0)/saline-EDTA (2.7 mM) containing deoxycholate. The buffer is made by adding 1.52 grams of deoxycholate to 50 ml of borate buffer/saline-EDTA. The phospholipid is dried on the surface of a glass tube and resuspended with borate/saline-EDTA/deoxycholate and vortexed to dissolve the lipid. The tube is incubated at 37° C. for 10 minutes and allowed to cool to 25° C. before use.

EXAMPLE 3

Assay to Test Perodixation of phospholipids in Presence of Peptides

The oxidation system consisted of a micelle substrate composed of 1-palmitoyl-2-linoleoylphosphatidycholine (3 mM) dispersed in borate (pH=9.0)/saline-EDTA (2.7 mM) and deoxycholate as described. Phospholipid micelles were used throughout most of these studies to optimize rates of lipid peroxidation catalyzed by specific enzymes. This permitted us to quantify initial rates reliably and in reproducible fashion. Soybean lipoxygenase (5 U/μl) and xanthine (0.2 mM)/xanthine oxidase (20 U/ml) were used to initiate lipid peroxidation following the addition of recombinant apolipoproteins to the phospholipid micelles. Increases in conjugated dienes (lipid peroxidation) were monitored by ultraviolet absorption spectroscopy (234 nm) at 25° C. The mass of phospholipid hydroperoxides was calculated using the molar absorptivity coefficient ($\epsilon=29{,}500$ Lcm$^{-1}$mol$^{-1}$) of conjugated dienes. This is made possible because the phospholipid used possesses only two carbon-carbon double bonds; as such, only one conjugated diene species is formed per phospholipid molecule. Initial rates of lipoxygenase mediated lipid peroxidation are calculated from the slopes of the linear portion of the oxidation curves and results can be expressed as nmoles of phospholipid peroxide formed/min.

Based on the maximum levels of lipid peroxide accumulation obtained in the absence of peptide (i.e. the plateau associated with the oxidation curves), it is possible to derive quantitative information regarding the potency of the peptide (i.e. the concentration of peptide resulting in 50% protection against lipid peroxidation). Thiol-containing peptides based on of apoA-I$_{Milano}$, apoA-I$_{Paris}$ and apoE3 generally give 50% protection at a concentration of 200 µg/ml.

EXAMPLE 4

Assays to Test Potential Interaction of Peptides with Other Water-soluble Anti-oxidants Interactions of between apoA-I$_{Milano}$ (and othe peptides) with reduced glutathione were evaluated using phospholipid micelles and lipoxygenase (5 U/µl). The latter initiates lipid peroxidation on phospholipid surfaces. Glutathione (GSH) is used a concentration which range from 0.025 to 0.1 mM which is added to the phospholipid micelles before the addition of lipoxygenase. GSH is also added in combination with A-I$_{Milano}$ (or its peptide mimetics) and lipid peroxidation monitored at 234 nm. The capacity of GSH plus apoA-I$_{Milano}$ (or other peptides) to inhibit lipid peroxidation is compared to the inhibitory action of the thiol-containing compounds alone. Water-soluble free radicals useful for this assay include but are not limited to any known biologically effective antioxidant, such as GSH, vitamin C, vitamin E and N-acetyl cysteine (NAC).

EXAMPLE 5

Assay to Test LCAT Activation Properties of Synthetic Peptides

ApoA-1 is a cofactor of LCAT which esterifies cholesterol on HDL. The ability of synthetic peptides to activate Lecithin:Cholesterol Acyltransferase (LCAT) was examined using a standard proteoliposome substrate (Chen and Alber, *J Lipid Res.* 23:680–691). The substrate contained the synthetic peptide of interest, phosphatidylcholine (egg yolk PC) and unesterfied cholesterol at the following mole ratios: 15:250:12.5. Trace amounts of [14C]cholesterol are added to the proteoliposome during preparation. To monitor cholesterol esterification, reaction mixtures are prepared with the following constituents, [14C]cholesterol containing proteoliposomes ($4.4 \times 10^5$ dpm/ml), 20 mM Tris (pH 8.0), 0.15 mM NaCl, 0.27 mM EDTA, 0.5% human serum albumin, 2.0 mM β-mercaptoethanol and recombinant human LCAT enzyme (20 µg/ml). Results are expressed as a percentage of [14C]cholesterol converted to [14C]cholesterol esters in a 30 minute assay at 37° C.

EXAMPLE 6

Assay to Determine Cellular Cholesterol Efflux Capability of the Peptides

The main function of ApoA-I is promoting cholesterol efflux from cells. This process results in formation of HDL particles. Therefore this assay is used to show that the peptides possess the native properties of apoA-I in promoting HDL assembly. The murine macrophage cell-line, J774, was used as cholesterol donors for efflux studies to lipid-free apolipoproteins or synthetic peptides. This cell-line was chosen because it has recently been shown to possess an active apolipoprotein-mediated efflux pathway involving ABCA1 which is up-regulated by the cAMP analog, 8-(4-chlorophenthio)adenosine 3':5'-cyclic monophosphate. Briefly, $1 \times 10^5$ cells/ml were seeded into 24 well culture plates and labeled with 1 µCi/ml of [3H]cholesterol dispersed in RMPI 1640 medium containing 1% FBS. Confluent monolayers of radio-labeled cells were equilibrated (2 h) with RPMI containing 0.2% BSA and extensively rinsed with serum-free RPMI prior to addition of recombinant apolipoproteins or synthetic peptides. In some instances 0.3 mM of the cAMP analog was added to serum-free medium to upregulate cellular cholesterol efflux. Lipid-free apolipoproteins and/or synthetic peptides were added (25 µg/ml) to serum-free RPMI and applied to cells. At specified times, aliquots of medium were removed and cellular debris pelleted by centrifugation (1000×g, 10 min). Results were expressed as a percentage of the initial cellular [3H]cholesterol appearing in the medium at each time point.

EXAMPLE 7

Assay Confirming that Peptides do not Quench Water Soluble Reactive Oxygen Species A stock solution (1 mg/ml) of cytochrome C is prepared and 50 µg/ml is added to 0.2 mM xanthine solution. Xanthine oxidase (20 U/ml) is added to generate water soluble reactive oxygen species (i.e. superoxide anion and hydroxyl radicals). Reduction of cytochrome C is followed at 550 nm over a time course to determine whether synthetic peptides directly quench the reactive oxygen species (ROS) in the absence of phospholipid.

The rate of reduction of cytochrome C was compared between X/Xo, X/Xo plus the control peptide (400 µg/ml), X/Xo plus the thiol-containing peptide (400 µg/ml) and SOD (superoxide dismutase) was used as a control. The synthetic peptides should fail to protect cytochrome C indicating that the thiol-containing peptide is unable to directly quench ROS in the aqueous phase.

EXAMPLE 8

Designing Peptides from Amphipathic Helices in ApoA-I$_{Milano}$

The following lists sequences of amino acids used to prepare peptides which exhibited the newly discovered anti-oxidant activity of apoA-I$_{Milano}$. Control sequences based on amphipathic alpha helices that lack cysteine residues are also listed. Alternative positions for the cysteine residues are listed for each sequence and are important both therapeutically and as biological tools to investigate the underlying basis of inflammatory related diseases.

Synthetic peptides based on the primary amino acid (aa) sequence (aa 167–184) where the R173C mutation can be found in apoA-I$_{Milano}$. SEQ ID NO: 1 mimics the precise location of the cysteine residue in apoA-I$_{Milano}$ SEQ ID NO: 2 is peptide based on wild-type apoA-I which lacks a cysteine residue. The underlined residues in SEQ ID NO: 2 represent alternative positions for the cysteine residue. SEQ ID NOS: 3–8 show peptides made with the underlined cysteine substitutions.

| | | |
|---|---|---|
| SDELRQCLAARLEALKEN | 167-R173C-184 | SEQ ID NO: 1 |
| SDELRQRLAARLEALKEN | Control wild type 167-184 | SEQ ID NO: 2 |
| SDELCQRLAARLEALKEN | 167-R171C-184 | SEQ ID NO: 3 |
| SDELRCLAARLEALKEN | 167-Q172C-184 | SEQ ID NO: 4 |
| SDELRQRCAARLEALKEN | 167-L174C-184 | SEQ ID NO: 5 |
| SDELRQRLCARLEALKEN | 167-R175C-184 | SEQ ID NO: 6 |
| SDELRQRLACRLEALKEN | 167-A176C-184 | SEQ ID NO: 7 |
| SDELRQRLAARLEACKEN | 167-L181C-184 | SEQ ID NO: 8 |

Synthetic peptides based on the primary amino acid sequence (145–162) where the R151C mutation can be found in apoA-I$_{Paris}$. The sequence in SEQ ID NO: 9 mimics the precise location of the cysteine residue in apoA-I$_{paris}$. SEQ ID NO: 10, sequence of control peptide based on wild-type apoA-I which lacks a cysteine residue. The underlined residues in SEQ ID NO: 10 represent alternative positions for the cysteine residue. The sequences in SEQ ID NOS: 11–15 are peptides made with the underlined cysteine substitutions.

| | | |
|---|---|---|
| GEEMRDCARAHVDALRTH | 145-R151C-162 | SEQ ID NO: 9 |
| GEEMRDRARAHVDALRTH | Control wild type 145-162 | SEQ ID NO: 10 |
| GEEMCDRARAHVDALRTH | 145-R149C-162 | SEQ ID NO: 11 |
| GEEMRCRARAHVDALRTH | 145-D150C-162 | SEQ ID NO: 12 |
| GEEMRDRCRAHVDALRTH | 145-A152C-162 | SEQ ID NO: 13 |
| GEEMRDRACAHVDALRTH | 145-R153C-162 | SEQ ID NO: 14 |
| GEEMRDRARACVDALRTH | 145-H155C-162 | SEQ ID NO: 15 |

Synthetic peptides based on amino acids 220–237 of wild-type apoA-I. SEQ ID NO: 16 lists a sequence that mimics the position of the cysteine residue at the polar/nonpolar interface of the amphipathic alpha helix as can be found in the apoA-I$_{Milano}$ based peptides (Line 1). SEQ ID NO: 17 corresponds to a control sequence based on wild-type apoA-I that lacks a cysteine residue. The underlined residues in SEQ ID NO: 17 represent alternative positions for the cysteine residues. The sequences in SEQ ID NOS: 18–29 are peptides made with the underlined cysteine substitutions.

| | | |
|---|---|---|
| PVLESFCVSFLSALEEYT | 220-K226C-237 | SEQ ID NO: 16 |
| PVLESFKVSFLSALEEYT | Control wild type 220-237 | SEQ ID NO: 17 |
| PVLCSFKVSFLSALEEYT | 220-E223C-237 | SEQ ID NO: 18 |
| PVLECFKVSFLSALEEYT | 220-S224C-237 | SEQ ID NO: 19 |
| PVLESCKVSFLSALEEYT | 220-F225C-237 | SEQ ID NO: 20 |
| PVLESFKCSFLSALEEYT | 220-V227C-237 | SEQ ID NO: 21 |
| PVLESFKVCFLSALEEYT | 220-S228C-237 | SEQ ID NO: 22 |
| PVLESFKVSCLSALEEYT | 220-F229C-237 | SEQ ID NO: 23 |
| PVLESFKVSFCSALEEYT | 220-L230C-237 | SEQ ID NO: 24 |
| PVLESFKVSFLCALEEYT | 220-S231C-237 | SEQ ID NO: 25 |
| PVLESFKVSFLSCLEEYT | 220-A232C-237 | SEQ ID NO: 26 |
| PVLESFKVSFLSALCEYT | 220-E234C-237 | SEQ ID NO: 27 |
| PVLESFKVSFLSALECYT | 220-E235C-237 | SEQ ID NO: 28 |
| PVLESFKVSFLSALEECT | 220-Y236C-237 | SEQ ID NO: 29 |

SEQ ID NO: 30 corresponds to amino acids 209–241 of wild-type apoA-I in which a cysteine has been added to the polar/nonpolar interface of the amphipathic alpha helix. This peptide possesses both the native cholesterol efflux properties of apoA-I (*J. Biol. Chem.* 274:2021–2028) and has been endowed with thiol dependent antioxidant activity. SEQ ID NO: 31 corresponds to a control peptide that lacks a cysteine residues. The underlined residues represents alternative sites for cysteine substitutions either singly or in combination to make new peptides. The core sequence is identical to that listed above (SEQ ID NO: 17) and the position of the cysteine residue follow those listed for SEQ ID NO: 18–29).

| | |
|---|---|
| PALEDLRQGLL PVLESFCVSFLSALEEYT KKLN | SEQ ID NO: 30 |
| PALEDLRQGLL PVLESFKVSFLSALEEYT KKLN | SEQ ID NO: 31 |

Synthetic peptides based on amino acids 44–61 of wild-type apoA-I. SEQ ID NO: 32 lists a sequence of a peptide containing a cysteine residue at the polar/nonpolar interface of the amphipathic alpha helix just as in apoA-I$_{Milano}$. SEQ ID NO: 33 corresponds to a control sequence based on wild-type apoA-I that lacks a cysteine residue. The underlined residues in SEQ ID NO: 33 represent alternative positions for the cysteine residue. SEQ ID NOS: 34–38 are peptides with the underlined cysteine substitutions.

| | | |
|---|---|---|
| LKLCDNWDSVTSTFSKLR | 44-L47C-61 | SEQ ID NO: 32 |
| LKLLDNWDSVTSTFSKLR | Control wild type 44-61 | SEQ ID NO: 33 |
| LCLLDNWDSVTSTFSKLR | 44-K45C-61 | SEQ ID NO: 34 |
| LKCLDNWDSVTSTFSKLR | 44-L46C-61 | SEQ ID NO: 35 |
| LKLLCNWDSVTSTFSKLR | 44-D48C-61 | SEQ ID NO: 36 |
| LKLLDCWDSVTSTFSKLR | 44-N49C-61 | SEQ ID NO: 37 |
| LKLLDNWDSVTSTFSCLR | 44-K59C-61 | SEQ ID NO: 38 |

Synthetic peptides based on a combination of helices (209–220 plus 44–65) found in wild-type apoA-I. SEQ ID NO: 39 lists the sequence of a peptide containing a cysteine residue located at the polar/nonpolar interface of an amphipathic alpha helix just as in apoA-I$_{Milano}$. SEQ ID NO: 40 corresponds to a control sequence based on wild-type apoA-I that lacks cysteine residues. The underlined residues in SEQ ID NO: 40 represent alternative positions for the cysteine residue. SEQ ID NOS: 41–46 are peptides with those underlined cysteine substitutions.

```
PALEDLRQGLLP LKLCDNWDSVTSTFSKLR  209/44-L47C-61      SEQ ID NO: 39

PALEDLRQGLLP LKLLDNWDSVTSTFSKLR  Control209/44-61    SEQ ID NO: 40

PALEDLCQGLLP LKLLDNWDSVTSTFSKLR  209-R215C-220/44-61 SEQ ID NO: 41

PALEDLRQGLLP LCLLDNWDSVTSTFSKLR  209/44-K45C-61      SEQ ID NO: 42

PALEDLRQGLLP LKCLDNWDSVTSTFSKLR  209/44-L46C-61      SEQ ID NO: 43

PALEDLRQGLLP LKLLCNWDSVTSTFSKLR  209/44-D48C-61      SEQ ID NO: 44

PALEDLRQGLLP LKLLDCWDSVTSTFSKLR  209/44-N49C-61      SEQ ID NO: 45

PALEDLRQGLLP LKLLDNWDSVTSTFSCLR  209/44--K59C-61     SEQ ID NO: 46
```

EXAMPLE 9

Amphipathic Antioxidant Peptide Based on Human Apolipoprotein E3

Synthetic peptides based on amino acids (105–122) of apoE3. The sequence in SEQ ID NO: 47 mimics the precise location of the cysteine residue in human apoE3. SEQ ID NO: 48 corresponds to a control peptide based on the primary amino acid sequence of apoE4 which lacks cysteine residues. The underlined residues in SEQ ID NO: 48 represent alternative positions for the cysteine residue. The sequences in SEQ ID NOS: 49–51 are peptides with those underlined cysteine substitutions.

```
GADMEDVCGRLVQYRGEV   105-R112C-122           SEQ ID NO: 47
GADMEDVRGRLVQYRGEV   Control wild type       SEQ ID NO: 48
                     105-122
GADMEDCRGRLVQYRGEV   105-V111C-122           SEQ ID NO: 49
GADMEDVRCRLVQYRGEV   105-G113C-122           SEQ ID NO: 50
GADMEDVRGCLVQYRGEV   105-R114C-122           SEQ ID NO: 51
```

EXAMPLE 10

Amphipathic Antioxidant Peptide Based on Apolipoprotein A-V

Synthetic peptides based on Apolipoprotein A-V. SEQ ID NO: 52 mimics the precise location of the cysteine residue in human apoAV amino acids 219–236. SEQ ID NO: 53 corresponds to a control peptide based on the same sequence as shown in SEQ ID NO: 52 except the cysteine residue has been replaced with a glycine residue to generate a peptide which lacks the cysteine. The underlined residues in SEQ ID NO: 53 represent alternative positions for the cysteine residue.

```
ARLSRCVQVLSRKLTLKA  219-G224C-236      SEQ ID NO: 52
ARLSRGVQVLSRKLTLKA  Control wild type  SEQ ID NO: 53
```

-continued
219-236

```
ARLCRGVQVLSRKLTLKA  219-S222C-236      SEQ ID NO: 54
ARLSCGVQVLSRKLTLKA  219-R223C-236      SEQ ID NO: 55
ARLSRGCVQVLSRKLTLKA 219-V225C-236      SEQ ID NO: 56
ARLSRGVQVLSRKCTLKA  219-L232C-236      SEQ ID NO: 57
```

SEQ ID NO: 58 lists a sequence of 36 amino acids (219–254) found in apoAV. SEQ ID NO: 59 is a control peptide based on peptide listed in SEQ ID NO: 58 except the cysteine has been replaced with a glycine residue. The underlined residues in SEQ ID NO: 58 represent alternative positions for the cysteine residue. SEQ ID NO: 60–63 are the peptides with the underlined cysteine substitutions.

```
ARLSRCVQVLSRKLTLKAKALHARIQQNLDQLREEL  219-G224C-254  SEQ ID NO: 58
ARLSRGVQVLSRKLTLKAKALHARIQQNLDQLREEL  Control        SEQ ID NO: 59
                                      219-254
ARLCRGVQVLSRKLTLKAKALHARIQQNLDQLREEL  219-S222C-254  SEQ ID NO: 60
ARLSCGVQVLSRKLTLKAKALHARIQQNLDQLREEL  219-R223C-254  SEQ ID NO: 61
ARLSRGCVQVLSRKLTLKAKALHARIQQNLDQLREEL 219-V225C-254  SEQ ID NO: 62
ARLSRGVQVLSRKCTLKAKALHARIQQNLDQLREEL  219-L232C-254  SEQ ID NO: 63
```

SEQ ID NO: 64 lists a sequence based on amino acids 51–72 of apoAV that has been engineered to possess a cysteine residue at the polar/nonpolar interface of the amphipathic alpha helix just as in apoA-I$_{Milano}$. The control peptide in SEQ ID NO: 65 does not contain a cysteine residue, but the underlined residues correspond to alternative sites for cysteine substitutions.

```
ATLKDSLCQDLNNMNKFLEKLR  51-E58C-72         SEQ ID NO: 64
ATLKDSLEQDLNNMNKFLEKLR  Control            SEQ ID NO: 65
                        wild type
                        51-72
ATLCDSLEQDLNNMNKFLEKLR  51-K54C-72         SEQ ID NO: 66
ATLKDCLEQDLNNMNKFLEKLR  51-S56C-72         SEQ ID NO: 67
ATLKDSCEQDLNNMNKFLEKLR  51-L57C-72         SEQ ID NO: 68
ATLKDSLECDLNNMNKFLEKLR  51-Q59C-72         SEQ ID NO: 69
ATLKDSLEQCLNNMNKFLEKLR  51-D60C-72         SEQ ID NO: 70
```

EXAMPLE 11

Peptide Based on Human Serum Paraoxonase

Human serum paraoxonase (PON1A) possesses thiol-dependent antioxidant activity, however, the domain structure of the enzyme is not well defined. It has been reported previously that the enzyme can inhibit lipoxygenase mediated lipid peroxidation (Brushia et al, *J. Lipid Res.* 42:951–958) utilizing the protocols set forth in the Examples which indicate that peptides derived from aspects of paraoxonase secondary structure may be useful in the design of therapeutic agents. Not shown is a two dimensional wheel projection of the synthetic peptide that encompasses the antioxidant domain of human serum paraoxonase. Amino acid residues 276–293 form an amphipathic alpha helix having a cysteine located at the interface of the hydrophilic/hydrophobic interface. Below is a brief list of peptides that possess beneficial potential as antioxidants. The sequences were derived from the basic criteria established in this patent disclosure including specific cysteine placement within amino acid stretches separated by proline residues. Moreover, the native PON enzyme is an HDL-associated protein that appears to possess thiol-dependent antioxidant activity directed toward lipid surfaces.

```
ETGDLWVGCHP                                SEQ ID NO: 71

ETGDLWVGCHPNGMKIFFYDSEN                    SEQ ID NO: 72

SEQ ID NO: 73
LKSLDFNTLVDNISVDP ETGDLWVGCHPNGMKIFFYDSEN
```

EXAMPLE 12

Amphipathic Antioxidant Peptide Based on a Generic Peptide

The sequence of the published (generic) peptide by Segrest et al., in U.S. Pat. No. 4,643,988, DWLKAFYDKVAEKLKEAF (SEQ ID NO:75), which codes for an alpha helix unrelated to apoA-I, can be modified for purposes of this invention. This peptide has been made to model apoA-I amphipathic alpha helices and used it extensively to study apoA-I structure and function (Yancey et al. Biochemistry, 1995, vol 34;7955–7965). Because it has been used often to study alpha helices, cysteine residues can be introduced into this peptide to model antioxidant activity in a generic sequence. SEQ ID NO: 74 is the Segrest peptide with a Cysteine placed at the interface. Alternate residues of cysteine substitution are underlined in control peptide SEQ ID NO: 75. SEQ ID NOS: 76–81 are peptides having those underlined cysteine substitutions.

```
DWLCAFYDKVAEKLKEAF    18A-K4C       SEQ ID NO: 74

DWLKAFYDKVAEKLKEAF    18A control   SEQ ID NO: 75

DCLKAFYDKVAEKLKEAF    18A-W2C       SEQ ID NO: 76

DWCKAFYDKVAEKLKEAF    18A-L3C       SEQ ID NO: 77

DWLKCFYDKVAEKLKEAF    18A-A5C       SEQ ID NO: 78

DWLKACYDKVAEKLKEAF    18A-F6C       SEQ ID NO: 79

DWLKAFYDKCAEKLKEAF    18A-V10C      SEQ ID NO: 80

DWLKAFYDKVCEKLKEAF    18A-A11C      SEQ ID NO: 81
```

EXAMPLE 13

Amphipathic Antioxidant Peptide Based on a Generic Peptide II

The following peptides are hypothetical in nature but were engineered to possess unique structural aspects of apoA-I (helix 1, aa 44–65) that may be important in promoting cellular cholesterol efflux, as well as, a cluster of arginine residues based on helix 6 (aa 145–166) that play a role in LCAT activation. Moreover, the antioxidant activity of apoA-$I_{Milano}$ has been added to the peptide by virtue of the placement of a free cysteine residue at the polar/nonploar interface of the first helical segment (18-mer).

The peptide is arranged in a series of two 18-mers separated by a proline residue. The first and second 18-mers contain a non-polar face composed entirely of leucine residues. Conservative substitutions in these domains for isoleucine, phenylalanine, tryptophan, and/or methionine residues can be made to increase the hydrophobicity of the peptide to facilitate lipid interactions. The polar face of this first 18-mer is modeled from helix 1 of apoA-I and it lacks salt-bridge interactions within the peptide and the overall net charge is zero. Cysteine placement at position 7 within the peptide mimics the position of the thiol at the polar/nonpolar interface of an amphipathic alpha helix as found in apoA-$I_{Milano}$, apoA-$I_{Paris}$ and apoE3. The second 18-mer connected in series via a proline residue is nearly an exact match to the first 18-mer except arginine residues have been added at positions 5 and 16 to mirror the precise arrangement of the conserved amino acids within helix 6 (aa 145–166) of apoA-I. The underlined serine residue can be replaced with a cysteine residue to add antioxidant properties to the second helical repeat.

The peptide can be used in combined form as shown in SEQ ID NO: 82 or as two singular 18-mers to separate biological activities. The underlined cysteine residue in SEQ ID NO: 83, can be replaced with a serine to remove thiol-dependent antioxidant activity. Conversely, thiol-dependent activity can be added to SEQ ID NO: 84 by replacing the serine with a cysteine residue. The unique feature of the peptides is the ability to precisely add or remove biological activities in a controlled manner to generate an array of biological tools to probe the complex etiology of inflammatory related diseases. This may permit the identification of specific biological activities that are most important in protecting against disease in various genetic models of atherosclerosis thus opening the door for the development of tailor-made pharmaceuticals to combat a variety of inflammatory diseases.

```
LEKLNSCLRDRLSALTDTPLEELRDSLRSRLDALRST  SEQ ID NO: 82

LEKLNSCLRDRLSALTDT                     SEQ ID NO: 83

LEELRDSLRSRLDALRST                     SEQ ID NO: 84
```

EXAMPLE 14

Antioxidant Activity of Synthetic Peptide Mimetics of apoA-$I_{Milano}$.

FIGS. 5A and 5B show the oxidation of phospholipid in the absence (squares) and presence of synthetic peptide mimetics based on apoA-$I_{Milano}$ and apoA-$I_{Paris}$, respectively. Oxidation of phospholipid was achieved by exposing phospholipid micelles to reactive oxygen specieis generated via xanthine/xanthine oxidase. Peptides based on apoA-$I_{Milano}$ (SEQ ID NO: 1) and apoA-$I_{Paris}$ (SEQ ID NO: 9) inhibited the oxidation of phospholipid in a dose dependent manner where diamonds, circles, triangles and hatched squares correspond to 100, 200, 300 and 400 µg/ml, respectively. Note that 50% protection was achieved with approximately 200 μg/ml of peptides derived from either apoA-I$_{Milano}$ or apoA-I$_{Paris}$.

FIG. 6A shows that a peptide which lacks a cysteine residue (167–184, SEQ ID NO: 2) failed to inhibit oxidation of phospholipid induced by reactive oxygen species. Peptide 167-R173C-184 based on apoA-I$_{Milano}$ effectively inhibited lipid peroxidation (FIG. 6B), but the thiol-containing peptide was unable to directly quench water-soluble reactive oxygen species in the aqueous phase as determined using the cytochrome C assay (FIG. 6C). This indicates that the antioxidant activity of the peptide mimetic of apoA-I$_{Milano}$ (SEQ ID NO: 1) was directed toward phospholipid similar to the full-length cysteine variant.

Phospholipid micelles were exposed to xanthine/xanthine oxidase (X/Xo, 20 U/ml) in the absence of peptide (squares, FIGS. 6A & 6B). FIG. 6A shows the results of a cysteine-free peptide (167–184) where diamonds, circles, triangles, and hatched squares correspond to 100, 200, 300 and 400 μml respectively. FIG. 6B shows results using the thiol-containing peptide (167-R173C-184); doses and symbols are the same as in FIG. 6A. FIG. 6C shows reduction of cytochrome C (no phospholipids) with X/Xo (squares); triangles, X/Xo plus the apoA-I$_{Milano}$ 167-R173C-184 peptide (400 μg/ml); circles, X/Xo plus the apoA-I$_{Milano}$ 167–184 peptide (400 μg/ml). Note the synthetic peptides failed to protect cytochrome C indicating that the thiol-containing apoA-I$_{Milano}$ peptide is unable to directly quench ROS in the aqueous phase. SOD (superoxide dismutase) was used as a control.

Figure 7:
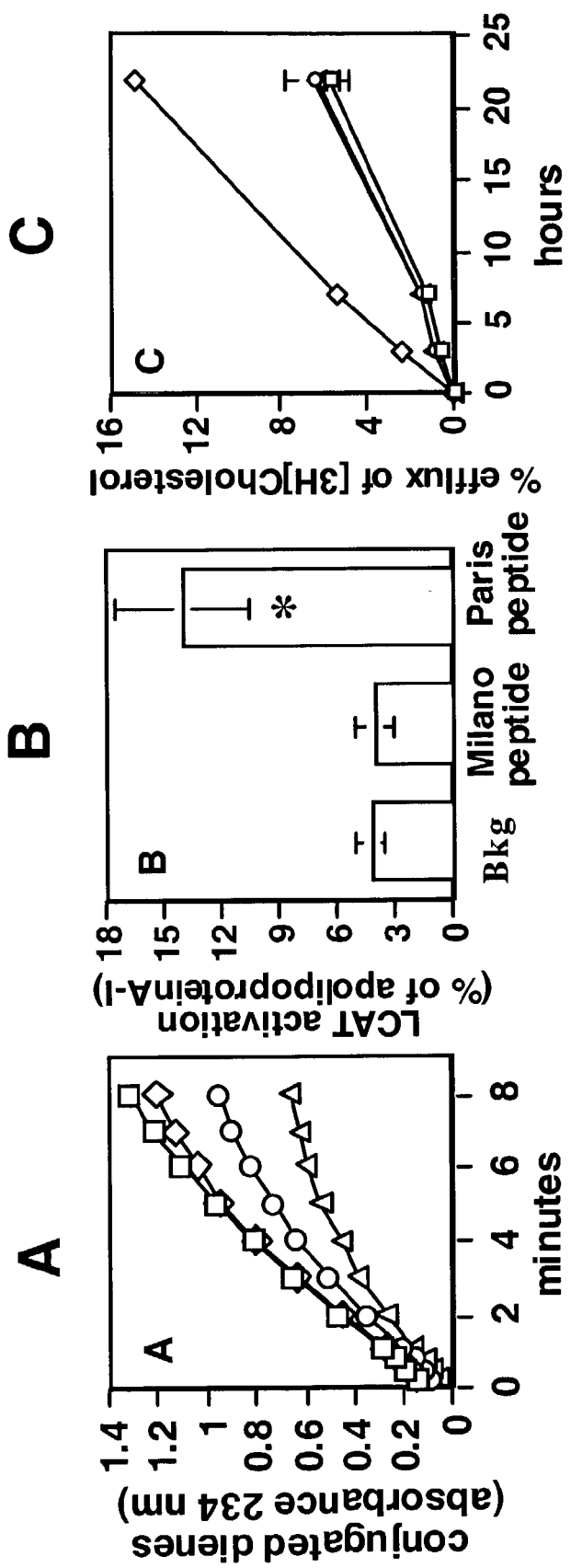
FIG. 7. Biological activities of synthetic apoA-I$_{Milano}$ peptide 167-R173C-184 (SEQ ID NO: 1) and synthetic apoA-I$_{Paris}$ peptide 145-R151C-162 (SEQ ID NO: 9).

Interaction of apoA-I$_{Milano}$ peptide 167-R173C-184 with GSH is shown in FIG. 7A. Squares show the oxidation of PL-micelles with lipoxygenase; diamonds, circles, and triangles correspond to oxidation in the presence of GSH alone (100 μM), peptide alone (200 μg/ml) and peptide plus GSH, respectively. FIG. 7A indicates that the apoA-I$_{Milano}$ peptide mimetic (SEQ ID NO: 1) was able to interact synergistically with reduced GSH to inhibit lipoxygenase-mediated lipid peroxidation. In the absence of thiol compound, lipoxygenase caused a rapid induction of lipid peroxidation (squares). The presence of reduced glutathione (0.1 mM, diamonds) was unable to effectively inhibit lipid peroxidation compared to incubations with the peptide mimetic of apoA-I$_{Milano}$ (200 μg/ml, circles). However, the combination of glutathione plus the peptide (triangles) provided even greater protection against oxidation compared to peptide alone.

FIG. 7B desmonstrates LCAT activation using a standard proteoliposome substrate composed of peptides: egg-yolk PC:unesterified cholesterol (15:250:12.5 mole ratios). Results are expressed as a percentage of activation obtained with apoA-I$_{WT}$. The synthetic peptide based on apoA-I$_{Paris}$ (SEQ ID NO: 9) was able to activate the ernzyme LCAT while the apoA-I$_{Milano}$ based peptide (SEQ ID NO: 1) failed in this regard (FIG. 7B). This is probably related to the cluster of three positively charged arginine residues (149, 153 and 160) associated with helix 6 (aa 145–162) of apoA-I that have been shown to play a role in LCAT activation. This series of arginine residues is present in the peptide based on apoA-I$_{Paris}$ but it is absent in the peptide based on apoA-I$_{Milano}$.

Both peptides based on apoA-I$_{Milano}$ and apoA-I$_{Paris}$ were unable to stimulate cholesterol efflux from J774 macrophages as shown in FIG. 7C. FIG. 7C: Cholesterol efflux from J774 macrophages; squares, serum free medium (□); circles, apoA-I$_{Milano}$ peptide (167-R173C-184, SEQ ID NO: 1) (○); triangles (behind squares), apoA-I$_{Paris}$ peptide (145-R151C-162, SEQ ID NO: 9) (Δ); diamonds, apoA-I$_{WT}$ (◊).

EXAMPLE 15

Antioxidant Activity of Synthetic Peptide Mimetics Based on Helix 10 of apoA-I

In FIG. 8A, PL micelles were exposed to lipoxygenase (5 U/μL) in the absence (squares) and presence of a synthetic peptide (220-E224C-237) based on helix 10 of apoA-I; diamonds, circles and triangles correspond to 100, 200, 300 μg/mL. For comparative purposes, the ability of peptide 167-R173C-184 to inhibit lipoxygenase-mediated lipid peroxidation is shown in FIG. 8B. Squares represent oxidation of phospholipid in the absence of peptide; diamonds, circles, triangles, and half-darkened squares correspond to 100, 200, 300, and 400 μg/ml of the apoA-I$_{Milano}$ based peptide, respectively. Note that both peptides inhibited lipid peroxidation over the same relative dose range indicating that incorporation of a cysteine residue within helix 10 of apoA-I, which is a Class Y amphipathic alpha helix, is able to confer antioxidant activity like the peptide mimetic of apoA-I$_{Milano}$.

EXAMPLE 16

Antioxidant Activity of Synthetic Peptide Mimetics of apoE3

Antioxidant activity of synthetic peptide, GADMED-VCGRLVQYRGEV (SEQ ID NO: 47), based on helix 3 of apolipoprotein E3 (apoE3) is shown in FIG. 9 . Phospholipid micelles were exposed to xanthine/xanthine oxidase (X/Xo, 20 U/ml) in the absence of peptide (squares, panels A & B). FIG. 9A shows the results of a cysteine-free peptide (105–122) based on the apolipoproteinE4 (apoE4) isoform where diamonds, circles, triangles, and hatched squares correspond to 100, 200, 300 and 400 μg/ml. . Note the control peptide (105–122, SEQ ID NO: 48) derived from apoE4 did not inhibit oxidation. FIG. 9B shows results using the thiol-containing peptide (105-R112C-122, SEQ ID NO: 47) based on apoE3; doses and symbols are the same as in FIG. 9A. In contrast to the peptide based on apoE4, peptide 105-R112C-122 based on apoE3 inhibited oxidation in a dose dependent manner similar to the peptides based on apoA-I$_{Milano}$ and apoA-I$_{Paris}$. FIG. 9C shows reduction of cytochrome C (no phospholopids) with X/Xo (squares); triangles X/Xo plus the apoE4 peptide (SEQ ID NO: 48) (400 μg/ml); circles, X/Xo plus the apoE3 peptide (SEQ ID NO: 47) (400 μg/ml). Note the synthetic peptides failed to protect cytochrome C indicating that the thiol-containing peptide (SEQ ID NO: 47) was unable to directly quench ROS in the aqueous phase. The asterisks denote the control SOD (superoxide dismutase).

The present examples, methods, procedures, treatments, specific compounds and molecules are meant to exemplify and illustrate the invention and should in no way be seen as limiting the scope of the invention. Any patents or publications mentioned in this specification are indicative of levels of those skilled in the art to which the patent pertains and are hereby incorporated by reference to the same extent as if each was specifically and individually incorporated by reference. The SEQUENCE LISTING accompanying this specification is also hereby incorporated by reference in its entirety.

What is claimed is:

1. A non-naturally occurring Apolipoprotein A-I (Apo A-I) peptide, the Apo A-I peptide comprising 18–100 amino acids and having an amphipathic alpha helix selected from the group consisting of: helix 1 (amino acids 44–61) of Apo A-I, and helix 9/10 (amino acids 209–241) of Apo A-I, wherein at least one native amino acid residue at or near the polar/nonpolar interface of said alpha helix is substituted with a cysteine, and wherein said cysteine substitution confers antioxidant activity to the peptide.

2. The Apo A-I peptide of claim 1, wherein the peptide is a modified helix 9/10 of Apo A-I and comprises the sequence:

PALEDLRQGLLPVLESFKVSFLSALEEYTKKLN (SEQ ID NO:31), and wherein the peptide has a cysteine residue substituted for any of one to four of the naturally occurring amino acids at positions 7, 16–24, and 26–27 of SEQ ID NO:31.

3. The Apo A-I peptide of claim 1, wherein the peptide is a modified helix 9/10 of Apo A-I and comprises the sequence:

PALEDLRQGLLPVLESFKVSFLSALEEYTKKLN (SEQ ID NO: 31),
and wherein said peptide has a cysteine residue substituted for the amino acid at position 18 of SEQ ID NO:31 (SEQ ID NO: 30).

4. The Apo A-I peptide of claim 1, wherein the peptide comprises from 18 to 40 amino acids.

5. The Apo A-I peptide of claim 1, wherein the peptide comprises from 18 to 20 amino acids.

6. The Apo A-I peptide of claim 1, wherein the antioxidant activity is inhibition of phospholipid oxidation.

* * * * *